(12) United States Patent
Chinta et al.

(10) Patent No.: US 12,264,124 B2
(45) Date of Patent: Apr. 1, 2025

(54) METHANOL PRODUCTION PROCESS FROM SYNGAS PRODUCED BY CATALYTIC PARTIAL OXIDATION INTEGRATED WITH CRACKING

(71) Applicant: ENI S.p.A., Rome (IT)

(72) Inventors: Sivadinarayana Chinta, Sugar Land, TX (US); Ravichander Narayanaswamy, Bengaluru (IN); Atul Pant, Bengaluru (IN)

(73) Assignee: ENI S.P.A., Rome (IT)

( * ) Notice: Subject to any disclaimer, the term of this patent is extended or adjusted under 35 U.S.C. 154(b) by 737 days.

(21) Appl. No.: 17/424,013

(22) PCT Filed: Dec. 31, 2019

(86) PCT No.: PCT/US2019/069067
§ 371 (c)(1),
(2) Date: Jul. 19, 2021

(87) PCT Pub. No.: WO2020/150005
PCT Pub. Date: Jul. 23, 2020

(65) Prior Publication Data
US 2022/0081380 A1    Mar. 17, 2022

Related U.S. Application Data

(60) Provisional application No. 62/793,606, filed on Jan. 17, 2019.

(51) Int. Cl.
*C07C 29/151* (2006.01)
*B01D 53/047* (2006.01)
(Continued)

(52) U.S. Cl.
CPC ........ *C07C 29/1518* (2013.01); *B01D 53/047* (2013.01); *B01D 53/229* (2013.01);
(Continued)

(58) Field of Classification Search
CPC ..... C07C 29/1518; C07C 5/333; C07C 5/327; C07C 29/76; C07C 29/80; B01D 53/047;
(Continued)

(56) References Cited

U.S. PATENT DOCUMENTS

| 6,903,139 B2 * | 6/2005 | Landis | C01B 3/386 |
| | | | 518/703 |
| 2007/0000176 A1 * | 1/2007 | Liu | C01B 3/48 |
| | | | 48/198.1 |

(Continued)

FOREIGN PATENT DOCUMENTS

| EP | 0112613 A2 | 7/1984 |
| WO | 2018202829 A1 | 11/2018 |

OTHER PUBLICATIONS

European Search Report for European Application No. 19910089.2, dated Sep. 15, 2022, 7 pages.
(Continued)

*Primary Examiner* — Andrew J. Oyer
(74) *Attorney, Agent, or Firm* — CANTOR COLBURN LLP

(57) ABSTRACT

A process for producing syngas and olefins including the steps of feeding a catalytic partial oxidation (CPO) reactant mixture (oxygen, first hydrocarbons, steam) to a CPO reactor (CPO catalyst); wherein the CPO reactant mixture reacts, via CPO reaction, in CPO reactor to produce a CPO reactor effluent ($H_2$, CO, $CO_2$, water, unreacted first hydrocarbons). The process further includes feeding a cracking unit feed (second hydrocarbons) to a cracking unit to produce a cracking unit product (olefins), a hydrogen-rich stream (hydrogen, $CH_4$), and a hydrocarbon recovery stream ($C_{4+}$ hydrocarbons); wherein the first and the second hydrocarbons are the same or different; recovering a hydrogen-enriched stream (hydrogen) and a hydrocarbon-enriched stream ($CH_4$) from the hydrogen-rich stream; and contacting (Continued)

the CPO reactor effluent with the hydrogen-enriched stream to yield hydrogen-enriched syngas, and wherein the M ratio (($H_2-CO_2$)/($CO+CO_2$)) of the hydrogen-enriched syngas is greater than the M ratio of the CPO reactor effluent.

9 Claims, 3 Drawing Sheets

(51) Int. Cl.
*B01D 53/22* (2006.01)
*C01B 3/38* (2006.01)
*C07C 5/333* (2006.01)
*F25J 1/00* (2006.01)

(52) U.S. Cl.
CPC .............. *C01B 3/382* (2013.01); *C07C 5/333* (2013.01); *B01D 2256/16* (2013.01); *B01D 2256/24* (2013.01); *B01D 2257/7022* (2013.01); *C01B 2203/0261* (2013.01); *C01B 2203/061* (2013.01); *C01B 2203/062* (2013.01); *C01B 2203/0833* (2013.01); *F25J 1/001* (2013.01)

(58) Field of Classification Search
CPC .............. B01D 53/229; B01D 2256/16; B01D 2256/24; B01D 2257/7022; C01B 3/382; C01B 2203/0261; C01B 2203/061; C01B 2203/062; C01B 2203/0833; C01B 3/26; C01B 2203/0283; C01B 2203/04; C01B 2203/141; C01B 3/386; F25J 1/001; C10G 2400/20; C10G 2400/22; C10G 11/18; C10G 2/32; Y02P 30/20; Y02P 30/40

See application file for complete search history.

(56) References Cited

U.S. PATENT DOCUMENTS

| | | |
|---|---|---|
| 2010/0074829 A1 | 3/2010 | Koss |
| 2011/0112314 A1 | 5/2011 | Chewter et al. |
| 2015/0087865 A1 | 3/2015 | Iaquaniello et al. |
| 2015/0336858 A1 | 11/2015 | Vicari et al. |
| 2017/0137355 A1 | 5/2017 | Sarsani et al. |
| 2018/0362418 A1 | 12/2018 | Mamedov et al. |

OTHER PUBLICATIONS

International Search Report issued Apr. 24, 2020 re: Application No. PCT/US2019/069067, pp. 1-3, citing: U.S. 2018-0362418 A1, U.S. 2010-0074829 A1, U.S. 2015-0336858 A1, WO 2018-202829 A1, EP 0112613 A2.

Written Opinion issued Apr. 24, 2020 re: Application No. PCT/US2019/069067, pp. 1-3, citing: U.S. 2018-0362418 A1, U.S. 2010-0074829 A1, U.S. 2015-0336858 A1, WO 2018-202829 A1, EP 0112613 A2.

\* cited by examiner

METHANOL PRODUCTION PROCESS FROM SYNGAS PRODUCED BY CATALYTIC PARTIAL OXIDATION INTEGRATED WITH CRACKING

TECHNICAL FIELD

The present disclosure relates to methods of producing methanol, more specifically methods of producing methanol from syngas produced by catalytic partial oxidation (CPO) of hydrocarbons, such as methane.

BACKGROUND

Synthesis gas (syngas) is a mixture comprising carbon monoxide (CO) and hydrogen ($H_2$), as well as small amounts of carbon dioxide ($CO_2$), water ($H_2O$), and unreacted methane ($CH_4$). Syngas is generally used as an intermediate in the production of methanol and ammonia, as well as an intermediate in creating synthetic petroleum to use as a lubricant or fuel. Syngas is produced conventionally by steam reforming of natural gas (steam methane reforming or SMR), although other hydrocarbon sources can be used for syngas production, such as refinery off-gases, naphtha feedstocks, heavy hydrocarbons, coal, biomass, etc. SMR is an endothermic process and requires significant energy input to drive the reaction forward. Conventional endothermic technologies such as SMR produce syngas with a $H_2$ content greater than the required content for methanol synthesis. Generally, SMR produces syngas with an M ratio ranging from 2.6 to 2.98, wherein the M ratio is a molar ratio defined as $(H_2-CO_2)/(CO+CO_2)$.

In an autothermal reforming (ATR) process, a portion of the natural gas is burned as fuel to drive the conversion of natural gas to syngas resulting in relatively low $H_2$ and high $CO_2$ concentrations. Conventional methanol production plants utilize a combined reforming (CR) technology that pairs SMR with autothermal reforming (ATR) to reduce the amount of $H_2$ present in syngas. ATR produces a syngas with a $H_2$ content lower than the required content for methanol synthesis. Generally, ATR produces syngas with an M ratio ranging from 1.7 to 1.84. In the CR technology, the natural gas feed volumetric flowrate to the SMR and the ATR can be adjusted to achieve an overall syngas M ratio of 2.0 to 2.06. Further, CR syngas has a $H_2$ content greater than the required content for methanol synthesis. Furthermore, SMR is a highly endothermic process, and the endothermicity of the SMR technology requires burning fuel to drive the syngas synthesis. Consequently, the SMR technology reduces the enemy efficiency of the methanol synthesis process.

Syngas can also be produced (non-commercially) by catalytic partial oxidation (CPO or CPOx) of natural gas. CPO processes employ partial oxidation of hydrocarbon feeds to syngas comprising CO and $H_2$. The CPO process is exothermic, thus eliminating the need for external heat supply. However, the composition of the produced syngas is not suitable for methanol synthesis, for example, owing to a reduced $H_2$ content. Further, maintaining a desired catalyst activity and productivity can be challenging in a CPO process, owing to elevated or run-away CPO temperatures leading to catalyst deactivation. The CPO reaction is exothermic, and can lead to a high temperature increase in a CPO catalyst bed, which can in turn lead to catalyst deactivation. Thus, there is an ongoing need for the development of syngas production via CPO processes that manage the reaction temperature, as well as produce a syngas that is suitable for a methanol production process.

BRIEF DESCRIPTION OF THE DRAWINGS

For a detailed description of the preferred aspects of the disclosed methods, reference will now be made to the accompanying drawing in which.

DETAILED DESCRIPTION

Figure 1:
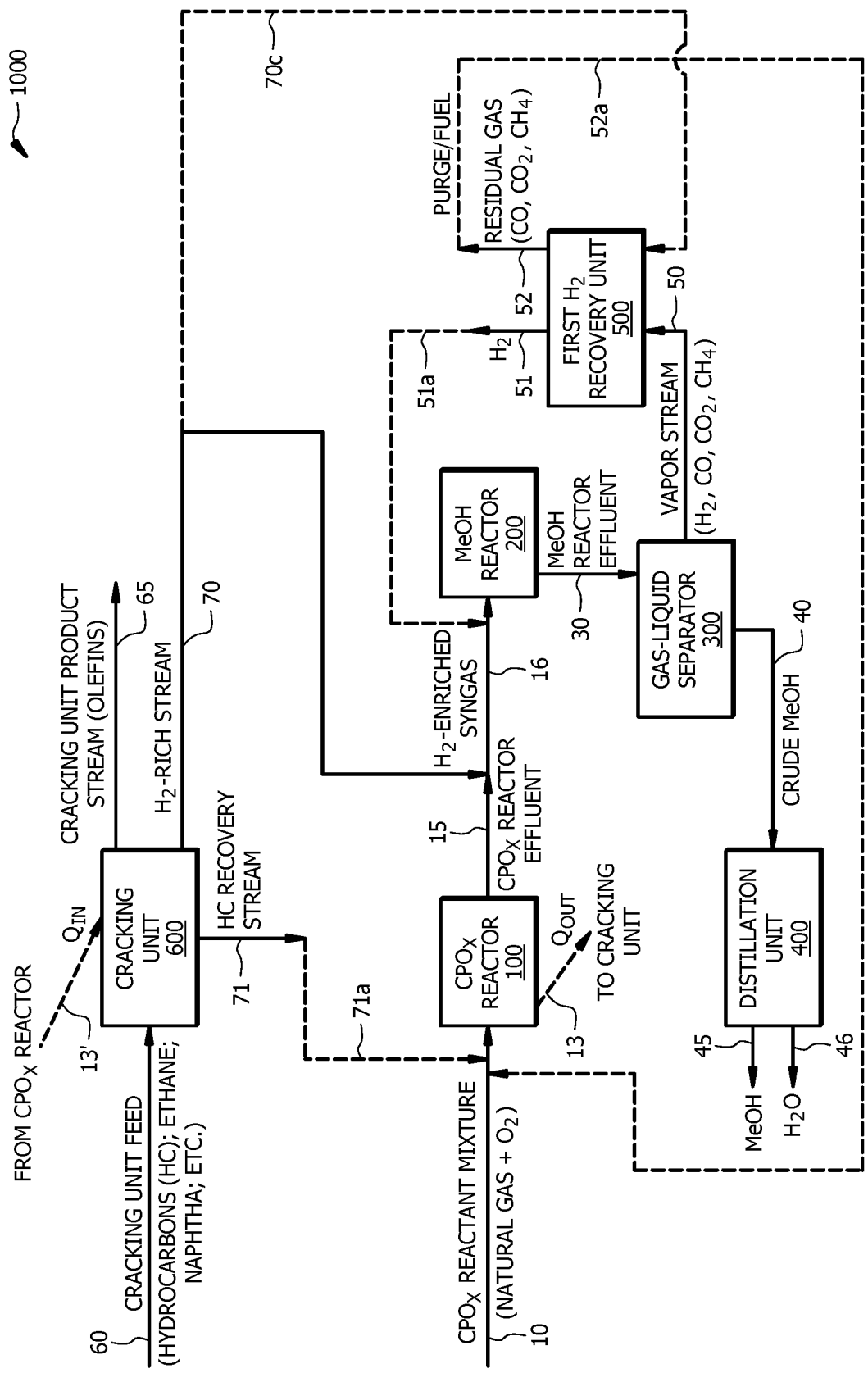
FIG. 1 displays a schematic of a system for a methanol production process.

Disclosed herein are processes for producing syngas and olefins comprising (a) feeding a catalytic partial oxidation (CPO or CPOx) reactant mixture to a CPO reactor; wherein the CPO reactant mixture comprises oxygen, first hydrocarbons, and optionally steam; wherein at least a portion of the CPO reactant mixture reacts, via a CPO reaction, in the CPO reactor to produce a CPO reactor effluent; wherein the CPO reactor comprises a CPO catalyst; wherein the CPO reactor effluent comprises hydrogen ($H_2$), carbon monoxide (CO), carbon dioxide ($CO_2$), water, and unreacted first hydrocarbons, and wherein the CPO reactor effluent is characterized by an M ratio of the CPO reactor effluent, wherein the M ratio is a molar ratio defined as $(H_2-CO_2)/(CO+CO_2)$; (b) feeding a cracking unit feed to a cracking unit to produce a cracking unit product stream, a hydrogen-rich stream, and a hydrocarbon recovery stream; wherein the cracking unit feed comprises second hydrocarbons; wherein the first hydrocarbons and the second hydrocarbons are the same or different; wherein the cracking unit product stream comprises olefins; wherein the hydrogen-rich stream comprises $H_2$, methane, and optionally unreacted second hydrocarbons; and wherein the hydrocarbon recovery stream comprises $C_{4+}$ hydrocarbons; and (c) contacting at least a portion of the CPO reactor effluent with at least a portion of the hydrogen-rich stream to yield hydrogen-enriched syngas, wherein the hydrogen-enriched syngas is characterized by an M ratio of the hydrogen-enriched syngas, and wherein the M ratio of the hydrogen-enriched syngas is greater than the M ratio of the CPO reactor effluent. In some aspects, the hydrogen-rich stream can be introduced to a hydrogen recovery unit to yield a hydrogen-enriched stream and a hydrocarbon-enriched stream, wherein the hydrogen-enriched stream can be further contacted with the CPO reactor effluent to yield the hydrogen-enriched syngas. The hydrocarbon recovery stream can be fed to the CPO reactor. The first hydrocarbons and/or the second hydrocarbons can comprise methane, ethane, propane, butanes, naptha, natural gas, natural gas liquids, associated gas, well head gas, enriched gas, paraffins, shale gas, shale liquids, fluid catalytic cracking (FCC) off gas, refinery process gases, stack gases, fuel gas from fuel gas header, or combinations thereof; and the olefins can comprise ethylene. The syngas can be further used in a methanol production process.

In order to adjust the $H_2/CO$ molar ratios of syngas to values greater than about 1.7-1.9, the processes disclosed herein illustrates methods for enhancing the $H_2/CO$ molar ratio and/or decrease the hydrocarbon concentration in syngas (e.g., decrease methane slip). In an aspect, a steam cracker off-gas that has a hydrogen-rich content can be blended with a CPO reactor effluent in any suitable proportions to provide for a hydrogen-enriched syngas having a $H_2/CO$ molar ratio of greater than about 2.0. In another aspect, a steam cracker off-gas that has a hydrogen-lean content can be mixed with fresh methane or natural gas and fed to the CPO reactor along with oxygen. In such aspect, residual $H_2$ present in the steam cracker off-gas can (1) increase the $H_2$ content of produced syngas, and/or (2) increase the reaction temperature in a CPO catalyst bed by $H_2$ combustion, wherein the elevated temperature increases the CPO reaction rate, as well as selectivity to CO and $H_2$. Run-away temperatures in the CPO reactor can be avoided by cracking ethane in coils immersed in a CPO catalyst bed. Process heat produced by the CPO reaction can be further used to crack ethane in coils positioned outside of the CPO catalyst bed.

Other than in the operating examples or where otherwise indicated, all numbers or expressions referring to quantities of ingredients, reaction conditions, and the like, used in the specification and claims are to be understood as modified in all instances by the term "about" Various numerical ranges are disclosed herein. Because these ranges are continuous, they include every value between the minimum and maximum values. The endpoints of all ranges reciting the same characteristic or component are independently combinable and inclusive of the recited endpoint. Unless expressly indicated otherwise, the various numerical ranges specified in this application are approximations. The endpoints of all ranges directed to the same component or property are inclusive of the endpoint and independently combinable. The term "from more than 0 to an amount" means that the named component is present in some amount more than 0, and up to and including the higher named amount.

The terms "a," "an," and "the" do not denote a limitation of quantity, but rather denote the presence of at least one of the referenced item. As used herein the singular forms "a," "an," and "the" include plural referents.

As used herein, "combinations thereof" is inclusive of one or more of the recited elements, optionally together with a like element not recited, e.g., inclusive of a combination of one or more of the named components, optionally with one or more other components not specifically named that have essentially the same function. As used herein, the term "combination" is inclusive of blends, mixtures, alloys, reaction products, and the like.

Reference throughout the specification to "an aspect," "another aspect," "other aspects," "some aspects," and so forth, means that a particular element (e.g., feature, structure, property, and/or characteristic) described in connection with the aspect is included in at least an aspect described herein, and may or may not be present in other aspects. In addition, it is to be understood that the described element(s) can be combined in any suitable manner in the various aspects.

As used herein, the terms "inhibiting" or "reducing" or "preventing" or "avoiding" or any variation of these terms, include any measurable decrease or complete inhibition to achieve a desired result. As used herein, the term "effective," means adequate to accomplish a desired, expected, or intended result. As used herein, the terms "comprising" (and any form of comprising, such as "comprise" and "comprises"), "having" (and any form of having, such as "have" and "has"), "including" (and any form of including, such as "include" and "includes") or "containing" (and any form of containing, such as "contain" and "contains") are inclusive or open-ended and do not exclude additional, unrecited elements or method steps.

Unless defined otherwise, technical and scientific terms used herein have the same meaning as is commonly understood by one of skill in the art. Compounds are described herein using standard nomenclature. For example, any position not substituted by any indicated group is understood to have its valency filled by a bond as indicated, or a hydrogen atom. A dash ("-") that is not between two letters or symbols is used to indicate a point of attachment for a substituent. For example, —CHO is attached through the carbon of the carbonyl group. As used herein, the terms "$C_x$ hydrocarbons" and "$C_x$s" are interchangeable and refer to any hydrocarbon having x number of carbon atoms (C). For example, the terms "$C_4$ hydrocarbons" and "$C_4$s" both refer to any hydrocarbons having exactly 4 carbon atoms, such as n-butane, iso-butane, cyclobutane, 1-butene, 2-butene, isobutylene, butadiene, and the like, or combinations thereof. As used herein, the term "$C_{x+}$ hydrocarbons" refers to any hydrocarbon having equal to or greater than x carbon atoms (C). For example, the term "$C_{2+}$ hydrocarbons" refers to any hydrocarbons having 2 or more carbon atoms, such as ethane, ethylene, $C_3$s, $C_4$s, $C_5$s, etc.

Figure 2:
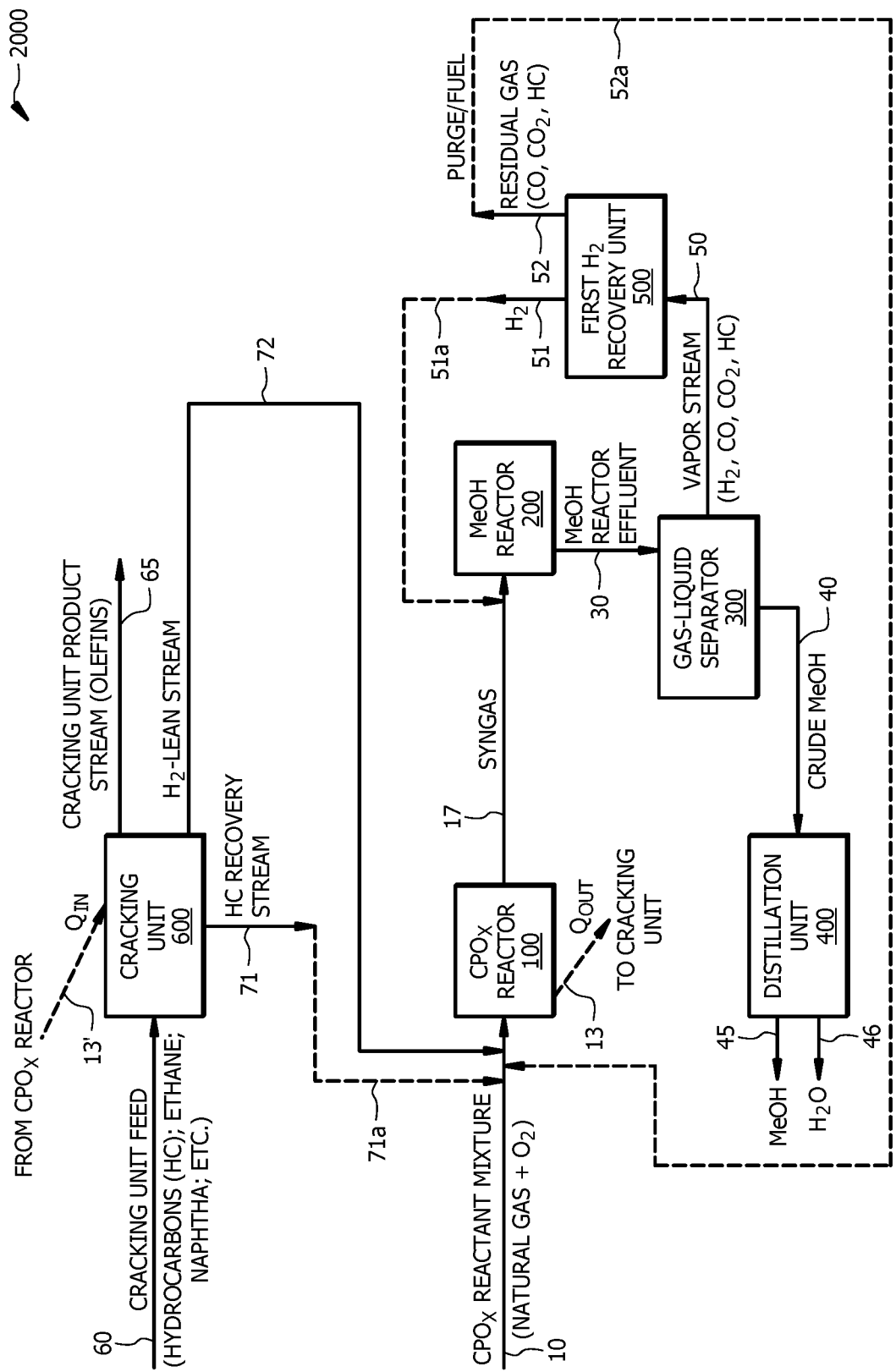
FIG. 2 displays a schematic of another system for a methanol production process.
Figure 3:
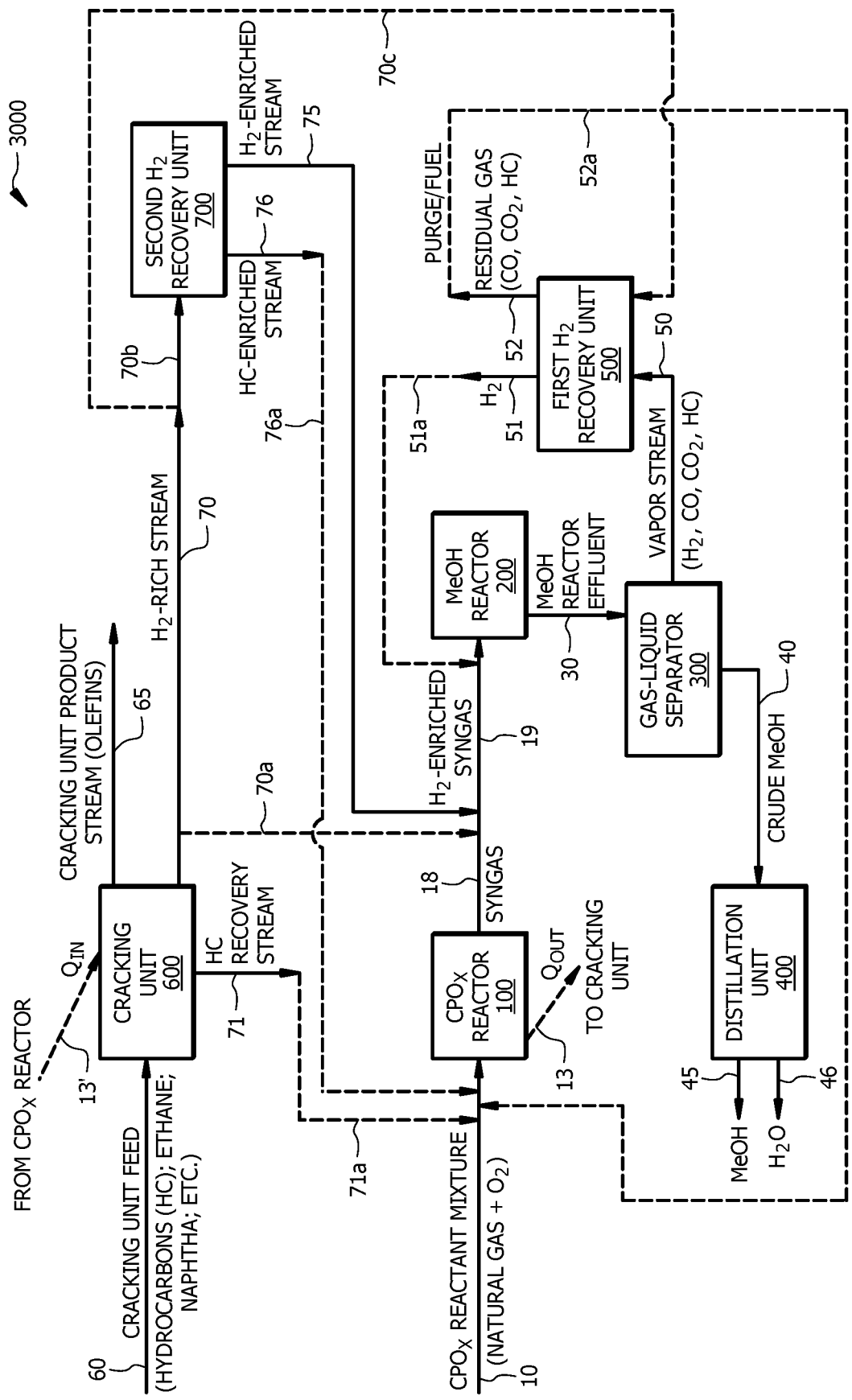
FIG. 3 displays a schematic of yet another system for a methanol production process.

Referring to FIG. 1, a methanol production system 1000 is disclosed. The methanol production system 1000 generally comprises a catalytic partial oxidation (CPO or CPOx) reactor 100; a methanol reactor 200; a gas-liquid separator 300; a distillation unit 400; a first hydrogen ($H_2$) recovery unit 500; and a cracking unit 600. Referring to FIG. 2, a methanol production system 2000 is disclosed. The methanol production system 2000 generally comprises a CPO reactor 100; a methanol reactor 200; a gas-liquid separator 300; a distillation unit 400; a first $H_2$ recovery unit 500; and a cracking unit 600. Referring to FIG. 3, a methanol production system 3000 is disclosed. The methanol production system 3000 generally comprises a CPO reactor 100; a methanol reactor 200; a gas-liquid separator 300; a distillation unit 400; a first $H_2$ recovery unit 500; a cracking unit 600; and a second $H_2$ recovery unit 700. As will be appreciated by one of skill in the art, and with the help of this disclosure, methanol production system components shown in FIGS. 1-3 can be in fluid communication with each other (as represented by the connecting lines indicating a direction of fluid flow) through any suitable conduits (e.g., pipes, streams, etc.). Common reference numerals refer to common components present in one or more of the Figures, and the description of a particular component is generally applicable across respective Figures wherein the component is present, except as otherwise indicated herein.

In an aspect, a process as disclosed herein can comprise a step of reacting, via a CPO reaction, a CPO reactant mixture 10 in the CPO reactor 100 to produce a CPO reactor effluent (e.g., syngas); wherein the CPO reactant mixture 10 comprises hydrocarbons (e.g., first hydrocarbons, second hydrocarbons) and oxygen; wherein the CPO reactor 100 comprises a CPO catalyst; and wherein the CPO reactor effluent (e.g., syngas) comprises hydrogen ($H_2$), carbon monoxide (CO), carbon dioxide ($CO_2$), water, and unreacted hydrocarbons (e.g., unreacted first hydrocarbons, unreacted second hydrocarbons). As will be appreciated by one of skill in the art, and with the help of this disclosure, depending on the composition of the CPO reactant mixture 10, the composition of the resulting CPO reactor effluent (e.g., syngas) recovered from the CPO reactor 100 can vary.

For example, and according to the configuration of the methanol production system 1000 in FIG. 1, the CPO reactant mixture can comprise $O_2$, first hydrocarbons, optionally at least a portion of a hydrocarbon recovery stream 71 (e.g., $C_{4+}$ hydrocarbons), and optionally steam;

and a CPO reactor effluent 15 can be recovered from CPO reactor 100, wherein the CPO reactor effluent 15 comprises $H_2$, $CO$, $CO_2$, water, and unreacted hydrocarbons (e.g., first hydrocarbons and optionally $C_{4+}$ hydrocarbons). As another example, and according to the configuration of the methanol production system 2000 in FIG. 2; the CPO reactant mixture can comprise $O_2$, first hydrocarbons, at least a portion of a hydrogen-lean stream 72 (e.g., $H_2$, $CH_4$, optionally second hydrocarbons such as $C_{2-3}$ hydrocarbons), optionally at least a portion of a hydrocarbon recovery stream 71 (e.g., $C_{4+}$ hydrocarbons), and optionally steam; and a syngas 17 can be recovered from the CPO reactor 100, wherein syngas 17 comprises $H_2$, $CO$, $CO_2$, water, and unreacted hydrocarbons (e.g., $CH_4$, first hydrocarbons, optionally second hydrocarbons, optionally $C_{4+}$ hydrocarbons). As yet another example, and according to the configuration of methanol production system 3000 in FIG. 3; the CPO reactant mixture can comprise oxygen, first hydrocarbons, optionally at least a portion of a hydrocarbon recovery stream 71 (e.g., $C_{4+}$ hydrocarbons), optionally at least a portion of a hydrocarbon-enriched stream 76 (e.g., methane, optionally second hydrocarbons such as $C_{2-3}$ hydrocarbons), and optionally steam; and a syngas 18 can be recovered from the CPO reactor 100, wherein syngas 18 comprises $H_2$, $CO$, $CO_2$, water, and unreacted hydrocarbons (e.g., first hydrocarbons, optionally methane, optionally second hydrocarbons, optionally $C_{4+}$ hydrocarbons).

Generally, the CPO reaction is based on partial combustion of fuels, such as various hydrocarbons, and in the case of methane, CPO can be represented by equation (1):

$$CH_4 + \tfrac{1}{2}O_2 \rightarrow CO + 2H_2 \quad (1)$$

Without wishing to be limited by theory, side reactions can take place along with the CPO reaction depicted in equation (1); and such side reactions can produce $CO_2$ and $H_2O$, for example via hydrocarbon combustion, which is an exothermic reaction. As will be appreciated by one of skill in the art, and with the help of this disclosure, and without wishing to be limited by theory, the CPO reaction as represented by equation (1) can yield a syngas with a hydrogen to carbon monoxide ($H_2/CO$) molar ratio having the theoretical stoichiometric limit of 2.0. Without wishing to be limited by theory, the theoretical stoichiometric limit of 2.0 for the $H_2/CO$ molar ratio means that the CPO reaction as represented by equation (1) yields 2 moles of $H_2$ for every 1 mole of CO, i.e., $H_2/CO$ molar ratio of (2 moles $H_2$/1 mole CO)=2. As will be appreciated by one of skill in the art, and with the help of this disclosure, the theoretical stoichiometric limit of 2.0 for the $H_2/CO$ molar ratio in a CPO reaction cannot be achieved practically because reactants (e.g., hydrocarbons, oxygen) as well as products (e.g., $H_2$, CO) undergo side reactions at the conditions used for the CPO reaction. As will be appreciated by one of skill in the art, and with the help of this disclosure, and without wishing to be limited by theory, in the presence of $O_2$, CO and $H_2$ can be oxidized to $CO_2$ and $H_2O$, respectively. The relative amounts (e.g., composition) of CO, $H_2$, $CO_2$ and $H_2O$ can be further altered by the equilibrium of the water-gas shift (WGS) reaction, which will be discussed in more detail later herein. The side reactions that can take place in CPO reactor 100 can have a direct impact on the M ratio of the produced syngas (e.g., CPO reactor effluent 15, syngas effluent; syngas 17; syngas 18), wherein the M ratio is a molar ratio defined as $(H_2-CO_2)/(CO+CO_2)$. In the absence of any side reaction (theoretically), the CPO reaction as represented by eqn. (1) results in a syngas with an M ratio of 2.0. However, the presence of side reactions (practically) reduces $H_2$ and increases $CO_2$, thereby resulting in a syngas with an M ratio below 2.0.

Further, without wishing to be limited by theory, the CPO reaction as depicted in equation (1) is an exothermic heterogeneous catalytic reaction (i.e., a mildly exothermic reaction) and it occurs in a single reactor unit, such as the CPO reactor 100 (as opposed to more than one reactor unit as is the case in conventional processes for syngas production, such as steam methane reforming (SMR)—autothermal reforming (ATR) combinations). While it is possible to conduct partial oxidation of hydrocarbons as a homogeneous reaction, in the absence of a catalyst, homogeneous partial oxidation of hydrocarbons process entails excessive temperatures, long residence times, as well as excessive coke formation, which strongly reduce the controllability of the partial oxidation reaction, and may not produce syngas of the desired quality in a single reactor unit. Furthermore, without wishing to be limited by theory, the CPO reaction is fairly resistant to chemical poisoning, and as such allows for the use of a wide variety of hydrocarbon feedstocks, including some sulfur containing hydrocarbon feedstocks; which, in some cases, can enhance catalyst life-time and productivity. By contrast, conventional ATR processes have more restrictive feed requirements, for example in terms of content of impurities in feed (e.g., feed to ATR is desulfurized), as well as hydrocarbon composition (e.g., ATR primarily uses a $CH_4$-rich feed).

In an aspect, the hydrocarbons (e.g., first hydrocarbons, second hydrocarbons) suitable for use in a CPO reaction as disclosed herein can include methane ($CH_4$), ethane, propane, butanes, naphtha, natural gas, natural gas liquids, associated gas, well head gas, enriched gas, paraffins, shale gas, shale liquids, fluid catalytic cracking (FCC) off gas, refinery process gases, stack gases, fuel gas from fuel gas header, and the like, or combinations thereof. The hydrocarbons (e.g., first hydrocarbons, second hydrocarbons) can include any suitable hydrocarbons source, and can contain $C_rC_6$ hydrocarbons, as well some heavier hydrocarbons.

In an aspect, the CPO reactant mixture 10 can comprise natural gas. Generally, natural gas is composed primarily of methane, but can also contain ethane, propane and heavier hydrocarbons (e.g., iso-butane, n-butane, iso-pentane, n-pentane, hexanes, etc.), as well as very small quantities of nitrogen ($N_2$), oxygen, $CO_2$, sulfur compounds, and/or water. The natural gas can be provided from a variety of sources including, but not limited to, gas fields, oil fields, coal fields, fracking of shale fields, biomass, landfill gas, and the like, or combinations thereof. In some aspects, the CPO reactant mixture 10 can comprise $CH_4$ and $O_2$.

The natural gas can comprise any suitable amount of methane. In some aspects, the natural gas can comprise biogas. For example, the natural gas can comprise from about 45 mol % to about 80 mol % methane, from about 20 mol % to about 55 mol % $CO_2$, and less than about 15 mol % $N_2$.

In an aspect, natural gas can comprise $CH_4$ in an amount of equal to or greater than about 45 mol %, about 50 mol %, about 55 mol %, about 60 mol %, about 65 mol %, about 70 mol %, about 75 mol %, about 80 mol %, about 82 mol %, about 84 mol %, about 86 mol %, about 88 mol %, about 90 mol %, about 91 mol %, about 92 mol %, about 93 mol %, about 94 mol %, about 95 mol %, about 96 mol %, about 97 mol %, about 98 mol %, or about 99 mol %.

In some aspects, the hydrocarbons (e.g., first hydrocarbons) suitable for use in a CPO reaction as disclosed herein can comprise $C_rC_6$ hydrocarbons, $N_2$ (e.g., from about 0.1 mol % to about 15 mol %, alternatively from about 0.5 mol % to about 11 mol %, alternatively from about 1 mol % to about 7.5 mol %, or alternatively from about 1.3 mol % to about 5.5 mol %), and $CO_2$ (e.g., from about 0.1 mol % to about 2 mol %, alternatively from about 0.2 mol % to about 1 mol %, or alternatively from about 0.3 mol % to about 0.6 mol %). For example, the hydrocarbons (e.g., first hydrocarbons) suitable for use in a CPO reaction as disclosed herein can comprise $C_1$ hydrocarbon (about 89 mol % to about 92 mol %); $C_2$ hydrocarbons (about 2.5 mol % to about 4 mol %); $C_3$ hydrocarbons (about 0.5 mol % to about 1.4 mol %); $C_4$ hydrocarbons (about 0.5 mol % to about 0.2 mol %); $C_5$ hydrocarbons (about 0.06 mol %); and $C_6$ hydrocarbons (about 0.02 mol %); and optionally $N_2$ (about 0.1 mol % to about 15 mol %), $CO_2$ (about 0.1 mol % to about 2 mol %), or both $N_2$ (about 0.1 mol % to about 15 mol %) and $CO_2$ (about 0.1 mol % to about 2 mol %).

The oxygen used in the CPO reactant mixture 10 can comprise 100% oxygen (substantially pure $O_2$), oxygen gas (which may be obtained via a membrane separation process), technical oxygen (which may contain some air), air, oxygen enriched air, oxygen-containing gaseous compounds (e.g., NO), oxygen-containing mixtures (e.g., $O_2/CO_2$, $O_2/H_2O$, $O_2/H_2O_2/H_2O$), oxy radical generators (e.g., $CH_3OH$, $CH_2O$), hydroxyl radical generators, and the like, or combinations thereof.

In an aspect, the CPO reactant mixture 10 can be characterized by a carbon to oxygen (C/O) molar ratio of less than about 3:1, alternatively less than about 2.6:1, alternatively less than about 2.4:1, alternatively less than about 2.2:1, alternatively less than about 2:1, alternatively less than about 1.9:1, alternatively equal to or greater than about 2:1, alternatively equal to or greater than about 2.2:1, alternatively equal to or greater than about 2.4:1, alternatively equal to or greater than about 2.6:1, alternatively from about 0.5:1 to about 3:1, alternatively from about 0.7:1 to about 2.5:1, alternatively from about 0.9:1 to about 2.2:1, alternatively from about 1:1 to about 2:1, alternatively from about 1.1:1 to about 1.9:1, alternatively from about 2:1 to about 3:1, alternatively from about 2.2:1 to about 3:1, alternatively from about 2.4:1 to about 3:1, or alternatively from about 2.6:1 to about 3:1, wherein the C/O molar ratio refers to the total moles of carbon (C) of hydrocarbons in the reactant mixture divided by the total moles of oxygen ($O_2$) in the reactant mixture. For example, when the only source of carbon in the CPO reactant mixture 10 is $CH_4$, the $CH_4/O_2$ molar ratio is the same as the C/0 molar ratio. As another example, when the CPO reactant mixture 10 contains other carbon sources besides $CH_4$, such as ethane ($C_2H_6$), propane ($C_3H_8$), butanes ($C_4H_{10}$), etc., the C/O molar ratio accounts for the moles of carbon in each compound (e.g., 2 moles of C in 1 mole of $C_2H_6$, 3 moles of C in 1 mole of $C_3H_8$, 4 moles of C in 1 mole of $C_4H_{10}$, etc.). As will be appreciated by one of skill in the art, and with the help of this disclosure, the C/O molar ratio in the CPO reactant mixture 10 can be adjusted along with other reactor process parameters (e.g., temperature, pressure, flow velocity, etc.) to provide for a syngas with a desired composition (e.g., a syngas with a desired $H_2/CO$ molar ratio; a syngas with a desired $CO_2$ content; etc.). The C/O molar ratio in the CPO reactant mixture 10 can be adjusted to provide for a decreased amount of unconverted hydrocarbons in the syngas. The C/O molar ratio in the CPO reactant mixture 10 can be adjusted based on the CPO effluent temperature in order to decrease (e.g., minimize) the unconverted hydrocarbons content of the syngas (e.g., CPO reactor effluent 15, syngas effluent; syngas 17; syngas 18). As will be appreciated by one of skill in the art, and with the help of this disclosure, when the syngas is further used in a methanol production process, unconverted hydrocarbons present in syngas can undesirably accumulate in a methanol reaction loop, thereby decreasing the efficiency of the methanol production process.

In an aspect, a portion of hydrocarbons (e.g., first hydrocarbons, second hydrocarbons) in CPO reactant mixture 10 can undergo a thermal decomposition reaction to carbon (C) and $H_2$, for example as represented by eqn. (2):

$$CH_4 \rightarrow C + 2H_2 \quad (2)$$

The decomposition reaction of hydrocarbons, such as methane, is facilitated by elevated temperatures, and increases the $H_2$ content in the CPO reactor effluent (e.g., syngas). As will be appreciated by one of skill in the art, and with the help of this disclosure, and without wishing to be limited by theory, while the percentage of hydrocarbons in the CPO reactant mixture 10 that undergoes a decomposition reaction (e.g., a decomposition reaction as represented by equation (2)) increases with increasing the C/O molar ratio in the CPO reactant mixture 10, a portion of hydrocarbons can undergo a decomposition reaction to C and $H_2$ even at relatively low C/O molar ratios in the CPO reactant mixture 10 (e.g., a C/O molar ratio in the CPO reactant mixture 10 of less than about 2:1).

The CPO reaction is an exothermic reaction (e.g., heterogeneous catalytic reaction; exothermic heterogeneous catalytic reaction) that is generally conducted in the presence of a CPO catalyst comprising a catalytically active metal, i.e., a metal active for catalyzing the CPO reaction. The catalytically active metal can comprise a noble metal (e.g., Pt, Rh, Ir, Pd, Ru, Ag, and the like, or combinations thereof); a non-noble metal (e.g., Ni, Co, V, Mo, P, Fe, Cu, and the like, or combinations thereof); rare earth elements (e.g., La, Ce, Nd, Eu, and the like, or combinations thereof); oxides thereof; and the like; or combinations thereof. Generally, a noble metal is a metal that resists corrosion and oxidation in a water-containing environment. As will be appreciated by one of skill in the art, and with the help of this disclosure, the components of the CPO catalyst (e.g., metals such as noble metals, non-noble metals, rare earth elements) can be either phase segregated or combined within the same phase.

In an aspect, the CPO catalysts suitable for use in the present disclosure can be supported catalysts and/or unsupported catalysts. In some aspects, the supported catalysts can comprise a support, wherein the support can be catalytically active (e.g., the support can catalyze a CPO reaction). For example, the catalytically active support can comprise a metal gauze or wire mesh (e.g., Pt gauze or wire mesh); a catalytically active metal monolithic catalyst; etc. In other aspects, the supported catalysts can comprise a support, wherein the support can be catalytically inactive (e.g., the support cannot catalyze a CPO reaction), such as $SiO_2$; silicon carbide (SiC); alumina; a catalytically inactive monolithic support; etc. In yet other aspects, the supported catalysts can comprise a catalytically active support and a catalytically inactive support.

In some aspects, a CPO catalyst can be wash coated onto a support, wherein the support can be catalytically active or inactive, and wherein the support can be a monolith, a foam, an irregular catalyst particle, etc.

In some aspects, the CPO catalyst can be a monolith, a foam, a powder, a particle, etc. Nonlimiting examples of CPO catalyst particle shapes suitable for use in the present disclosure include cylindrical, discoidal, spherical, tabular, ellipsoidal, equant, irregular, cubic, acicular, and the like, or combinations thereof.

In some aspects, the support comprises an inorganic oxide, alpha, beta or theta alumina ($Al_2O_3$), activated $Al_2O_3$, silicon dioxide ($SiO_2$), titanium dioxide ($TiO_2$), magnesium oxide (MgO), zirconium oxide ($ZrO_2$), lanthanum (III) oxide ($La_2O_3$), yttrium (III) oxide ($Y_2O_3$), cerium (IV) oxide ($CeO_2$), zeolites, ZSM-5, perovskite oxides, hydrotalcite oxides, and the like, or combinations thereof.

CPO processes, CPO reactors, CPO catalysts, and CPO catalyst bed configurations suitable for use in the present disclosure are described in more detail in U.S. Provisional Patent Application No. 62/522,910 filed Jun. 21, 2017 (International Application No. PCT/IB2018/054475 filed Jun. 18, 2018) and entitled "Improved Reactor Designs for Heterogeneous Catalytic Reactions;" and U.S. Provisional Patent Application No. 62/521,831 filed Jun. 19, 2017 (International Application No. PCT/IB2018/054470 filed Jun. 18, 2018) and entitled "An Improved Process for Syngas Production for Petrochemical Applications;" each of which is incorporated by reference herein in its entirety.

In an aspect, a CPO reactor suitable for use in the present disclosure (e.g., CPO reactor 100) can comprise a tubular reactor, a continuous flow reactor, a fixed bed reactor, a fluidized bed reactor, a moving bed reactor, a riser type reactor, a bubbling bed reactor, a circulating bed reactor, an ebullated bed reactor, a rotary kiln reactor, and the like, or combinations thereof.

In some aspects, the CPO reactor 100 can be characterized by at least one CPO operational parameter selected from the group consisting of a CPO reactor temperature (e.g., CPO catalyst bed temperature); CPO feed temperature (e.g., CPO reactant mixture temperature); target CPO effluent temperature; a CPO pressure (e.g., CPO reactor pressure); a CPO contact time (e.g., CPO reactor contact time); a C/O molar ratio in the CPO reactant mixture; a steam to carbon (S/C) molar ratio in the CPO reactant mixture, wherein the S/C molar ratio refers to the total moles of water ($H_2O$) in the reactant mixture divided by the total moles of carbon (C) of hydrocarbons in the reactant mixture; and combinations thereof. For purposes of the disclosure herein, the CPO effluent temperature is the temperature of the syngas (e.g., CPO reactor effluent 15, syngas effluent; syngas 17; syngas 18) measured at the point where the syngas exits the CPO reactor (CPO reactor 100), e.g., a temperature of the syngas measured at a CPO reactor outlet, a temperature of the syngas effluent, a temperature of the exit syngas effluent. For purposes of the disclosure herein, the CPO effluent temperature (e.g., target CPO effluent temperature) is considered an operational parameter. As will be appreciated by one of skill in the art, and with the help of this disclosure, the choice of operational parameters for the CPO reactor such as CPO feed temperature; CPO pressure; CPO contact time; C/O molar ratio in the CPO reactant mixture; S/C molar ratio in the CPO reactant mixture; etc. determines the temperature of the syngas effluent (e.g., CPO reactor effluent 15, syngas effluent; syngas 17; syngas 18), as well as the composition of the syngas effluent (e.g., CPO reactor effluent 15, syngas effluent; syngas 17; syngas 18). Further, and as will be appreciated by one of skill in the art, and with the help of this disclosure, monitoring the CPO effluent temperature can provide feedback for changing other operational parameters (e.g., CPO feed temperature; CPO pressure; CPO contact time; C/O molar ratio in the CPO reactant mixture; S/C molar ratio in the CPO reactant mixture; etc.) as necessary for the CPO effluent temperature to match the target CPO effluent temperature. Furthermore, and as will be appreciated by one of skill in the art, and with the help of this disclosure, the target CPO effluent temperature is the desired CPO effluent temperature, and the CPO effluent temperature (e.g., measured CPO effluent temperature, actual CPO effluent temperature) may or may not coincide with the target CPO effluent temperature. In aspects where the CPO effluent temperature is different from the target CPO effluent temperature, one or more CPO operational parameters (e.g., CPO feed temperature; CPO pressure; CPO contact time; C/O molar ratio in the CPO reactant mixture; S/C molar ratio in the CPO reactant mixture; etc.) can be adjusted (e.g., modified) in order for the CPO effluent temperature to match (e.g., be the same with, coincide with) the target CPO effluent temperature. The CPO reactor 100 can be operated under any suitable operational parameters that can provide for a syngas with a desired composition (e.g., a syngas with a desired $H_2/CO$ molar ratio; a syngas with a desired $CO_2$ content; etc.).

The CPO reactor 100 can be characterized by a CPO feed temperature of from about 25° C. to about 600° C., alternatively from about 25° C. to about 500° C., alternatively from about 25° C. to about 400° C., alternatively from about 50° C. to about 400° C., or alternatively from about 100° C. to about 400° C. In aspects where the CPO reactant mixture comprises steam, the CPO feed temperature can be as high as about 600° C., about 575° C., about 550° C., or about 525° C. In aspects where the CPO reactant mixture does not comprise steam, the CPO feed temperature can be as high as about 450° C., about 425° C., about 400° C., or about 375° C. The CPO reactor 100 can be characterized by a CPO effluent temperature (e.g., target CPO effluent temperature) of equal to or greater than about 300° C., about 600° C., about 700° C., about 750° C., about 800° C., or about 850° C., alternatively from about 300° C. to about 1,600° C., alternatively from about 600° C. to about 1,400° C., alternatively from about 600° C. to about 1,300° C., alternatively from about 700° C. to about 1,200° C., alternatively from about 750° C. to about 1,150° C., alternatively from about 800° C. to about 1,125° C., or alternatively from about 850° C. to about 1,100° C.

In an aspect, the CPO reactor 100 can be characterized by any suitable reactor temperature and/or catalyst bed temperature. For example, the CPO reactor 100 can be characterized by a reactor temperature and/or catalyst bed temperature of equal to or greater than about 300° C., about 600° C., about 700° C., about 750° C., about 800° C., or about 850° C., alternatively from about 300° C. to about 1,600° C., alternatively from about 600° C. to about 1,400° C., alternatively from about 600° C. to about 1,300° C., alternatively from about 700° C. to about 1,200° C., alternatively from about 750° C. to about 1,150° C., alternatively from about 800° C. to about 1,125° C., or alternatively from about 850° C. to about 1,100° C.

The CPO reactor 100 can be operated under any suitable temperature profile that can provide for a syngas with a desired composition (e.g., a syngas with a desired $H_2/CO$ molar ratio; a syngas with a desired $CO_2$ content; etc.). The CPO reactor 100 can be operated under adiabatic conditions, non-adiabatic conditions, isothermal conditions, near-isothermal conditions, etc. For purposes of the disclosure herein, the term "non-adiabatic conditions" refers to process conditions wherein a reactor is subjected to external heat exchange or transfer (e.g., the reactor is heated; or the reactor is cooled), which can be direct heat exchange and/or indirect heat exchange. As will be appreciated by one of skill in the art, and with the help of this disclosure, the terms "direct heat exchange" and "indirect heat exchange" are known to one of skill in the art. By contrast, the term "adiabatic conditions" refers to process conditions wherein a reactor is not subjected to external heat exchange (e.g., the reactor is not heated; or the reactor is not cooled). Generally, external heat exchange implies an external heat exchange system (e.g., a cooling system; a heating system) that requires energy input and/or output. As will be appreciated by one of skill in the art, and with the help of this disclosure, external heat transfer can also result from heat loss from the catalyst bed (or reactor) owing to radiation heat transfer, conduction heat transfer, convection heat transfer, and the like, or combinations thereof. For example, the catalyst bed can participate in heat exchange with the external environment, and/or with reactor zones upstream and/or downstream of the catalyst bed.

For purposes of the disclosure herein, the term "isothermal conditions" refers to process conditions (e.g., CPO operational parameters) that allow for a substantially constant temperature of the reactor and/or catalyst bed (e.g., isothermal temperature) that can be defined as a temperature that varies by less than about ±10° C., about ±9° C., about ±8° C., about ±7° C., about ±6° C., about ±5° C., about ±4° C., about ±3° C., about ±2° C., or about ±1° C. across the reactor and/or catalyst bed, respectively. Further, for purposes of the disclosure herein, the term "isothermal conditions" refers to process conditions (e.g., CPO operational parameters) effective for providing for a syngas with a desired composition (e.g., a desired $H_2/CO$ molar ratio; a desired $CO_2$ content; etc.), wherein the isothermal conditions comprise a temperature variation of less than about ±10° C. across the reactor and/or catalyst bed. The CPO reactor 100 can be operated under any suitable operational parameters that can provide for isothermal conditions.

For purposes of the disclosure herein, the term "near-isothermal conditions" refers to process conditions (e.g., CPO operational parameters) that allow for a fairly constant temperature of the reactor and/or catalyst bed (e.g., near-isothermal temperature), which can be defined as a temperature that varies by less than about ±100° C., about ±90° C., about ±80° C., about ±70° C., about ±60° C., about ±50° C., about ±40° C., about ±30° C., about ±20° C., about ±10° C., about ±9° C., about ±8° C., about ±7° C., about ±6° C., about ±5° C., about ±4° C., about ±3° C., about ±2° C., or about ±1° C. across the reactor and/or catalyst bed, respectively. In some aspects, near-isothermal conditions allow for a temperature variation of less than about ±50° C., alternatively less than about ±25° C., or alternatively less than about ±10° C. across the reactor and/or catalyst bed. Further, for purposes of the disclosure herein, the term "near-isothermal conditions" is understood to include "isothermal" conditions.

Furthermore, for purposes of the disclosure herein, the term "near-isothermal conditions" refers to process conditions (e.g., CPO operational parameters) effective for providing for a syngas with a desired composition (e.g., a desired $H_2/CO$ molar ratio; a desired $CO_2$ content; etc.), wherein the near-isothermal conditions comprise a temperature variation of less than about +100° C. across the reactor and/or catalyst bed.

In an aspect, a process as disclosed herein can comprise conducting the CPO reaction under near-isothermal conditions to produce syngas, wherein the near-isothermal conditions comprise a temperature variation of less than about ±100° C. across the reactor and/or catalyst bed. The CPO reactor 100 can be operated under any suitable operational parameters that can provide for near-isothermal conditions. Near-isothermal conditions can be provided by a variety of process and catalyst variables, such as temperature (e.g., heat exchange or heat transfer), pressure, gas flow rates, reactor configuration, catalyst bed configuration, catalyst bed composition, reactor cross sectional area, feed gas staging, feed gas injection, feed gas composition, and the like, or combinations thereof. Without wishing to be limited by theory, the terms "heat transfer" or "heat exchange" refer to thermal energy being exchanged or transferred between two systems (e.g., two reactors, such as CPO reactor and cracking reactor), and the terms "heat transfer" or "heat exchange" are used interchangeably for purposes of the disclosure herein.

In some aspects, achieving a target CPO effluent temperature and/or near-isothermal conditions can be provided by heat exchange or heat transfer. The heat exchange can comprise heating the reactor; or cooling the reactor. In an aspect, achieving a target CPO effluent temperature and/or near-isothermal conditions can be provided by cooling the reactor. In another aspect, achieving a target CPO effluent temperature and/or near-isothermal conditions can be provided by heating the reactor. In some aspects, achieving a target CPO effluent temperature and/or near-isothermal conditions can be provided by direct heat exchange and/or indirect heat exchange. As will be appreciated by one of skill in the art, and with the help of this disclosure, the terms "direct heat exchange" and "indirect heat exchange" are known to one of skill in the art. The heat exchange can comprise external heat exchange, external coolant fluid cooling, reactive cooling, liquid nitrogen cooling, cryogenic cooling, electric heating, electric arc heating, microwave heating, radiant heating, natural gas combustion, solar heating, infrared heating, use of a diluent in the CPO reactant mixture, and the like, or combinations thereof. For example, reactive cooling can be effected by carrying out an endothermic reaction in a cooling coil/jacket associated with (e.g., located in) the reactor.

In some aspects, achieving a target CPO effluent temperature and/or near-isothermal conditions can be provided by removal of process heat from the CPO reactor. In other aspects, achieving a target CPO effluent temperature and/or near-isothermal conditions can be provided by supplying heat to the CPO reactor. As will be appreciated by one of skill in the art, and with the help of this disclosure, a CPO reactor may need to undergo both heating and cooling in order to achieve a target CPO effluent temperature and/or near-isothermal conditions.

In an aspect, the heat exchange or heat transfer can comprise introducing a cooling agent, such as a diluent, into the reactor (e.g., CPO reactor 100), to decrease the reactor temperature and/or the catalyst bed temperature, while increasing a temperature of the cooling agent and/or changing the phase of the cooling agent. The cooling agent can be reactive or non-reactive. The cooling agent can be in liquid state and/or in vapor state. As will be appreciated by one of skill in the art, and with the help of this disclosure, the cooling agent can act as a flammability retardant; for example by reducing the temperature inside the reactor, by changing the gas mixture composition, by reducing the combustion of hydrocarbons to $CO_2$; etc.

In some aspects, CPO reactant mixture 10 can further comprise a diluent, wherein the diluent contributes to achieving a target CPO effluent temperature and/or near-isothermal conditions via heat exchange, as disclosed herein. The diluent can comprise water, steam, inert gases (e.g., argon), $N_2$, $CO_2$, and the like, or combinations thereof. Generally, the diluent is inert with respect to the CPO reaction, e.g., the diluent does not participate in the CPO reaction. However, and as will be appreciated by one of skill in the art, and with the help of this disclosure, some diluents (e.g., water, steam, $CO_2$, etc.) might undergo chemical reactions other than the CPO reaction within the reactor, and can change the composition of the resulting syngas, as will be described in more detail later herein; while other diluents (e.g., $N_2$, argon (Ar)) might not participate in reactions that change the composition of the resulting syngas. As will be appreciated by one of skill in the art, and with the help of this disclosure, the diluent can be used to vary the composition of the resulting syngas. The diluent can be present in CPO reactant mixture 10 in any suitable amount.

In an aspect, achieving a target CPO effluent temperature and/or near-isothermal conditions can be provided by removal of process heat ($Q_{out}$) from the CPO reactor 100, e.g., cooling the CPO reactor 100, for example by heating a cracking reactor and/or heating water to produce steam. As will be appreciated by one of skill in the art, and with the help of this disclosure, a positive Q going "out" (by the direction of the arrow 13) represents that heat is being transferred from that particular reactor, e.g., that particular reactor is being cooled. For example, Qou, 13 in FIGS. 1-3 indicate that heat is being transferred from the CPO reactor 100 (e.g., the CPO reactor 100 is being cooled), for example to a cracking process and/or a steam production process, respectively. As will be appreciated by one of skill in the art, and with the help of this disclosure, a positive Q going "in" (by the direction of the arrow 13') represents heat being transferred to that particular system/unit/reactor, e.g., that particular system/unit/reactor is being heated.

In some aspects, the heat transfer can comprise cooling the CPO reactor 100 while heating a cracking reactor (e.g., a cracking reactor in cracking unit 600), wherein the cracking reactor can optionally produce ethylene by ethane cracking. In an aspect, a cracking unit feed 60 can be fed to the cracking reactor, wherein the cracking unit feed comprises second hydrocarbons, such as alkanes (e.g., ethane, propane, butanes, naphtha, and the like, or combinations thereof); wherein at least a portion of the second hydrocarbons undergoes an endothermic cracking reaction in the cracking reactor to produce a cracking reactor product stream; and wherein the cracking reactor product stream comprises olefins (e.g., ethylene), hydrogen, and unreacted alkanes. In other aspects, the heat transfer can comprise cooling the CPO reactor 100 while heating water to produce steam. In some aspects, the CPO reactor 100 can comprise a water-cooled reactor. The CPO reactor 100 can have internal and/or external cooling elements for water to steam conversion. For example, conduits for water to steam conversion can be used as internal cooling elements in the CPO reactor 100, wherein a portion of the process heat from the CPO reaction heats the water inside such conduits, thereby converting the water to steam. As another example, a cooling external jacket can be used for water to steam conversion. Heat transfer integration of a CPO process with a cracking process and/or steam production process is described in more detail in U.S. Provisional Patent Application Nos. 62/787,620 filed Jan. 2, 2019 and entitled "Catalyst Activity Management in Catalytic Partial Oxidation" and 62/810,629 filed Feb. 26, 2019 and entitled "An Integrated Process for the Production of Syngas and Olefins by Catalytic Partial Oxidation and Cracking"); each of which is incorporated by reference herein in its entirety.

In some aspects, the heat transfer (e.g., heat transfer that provides for achieving a target CPO effluent temperature and/or near-isothermal conditions) excludes heat transfer with the syngas effluent (e.g., CPO reactor effluent 15, syngas effluent; syngas 17; syngas 18) subsequent to the syngas effluent (e.g., CPO reactor effluent 15, syngas effluent; syngas 17; syngas 18) exiting the CPO reactor (e.g., CPO reactor 100). In other aspects, the heat transfer (e.g., heat transfer that provides for achieving a target CPO effluent temperature and/or near-isothermal conditions) can comprise heat transfer with the syngas effluent (e.g., CPO reactor effluent 15, syngas effluent; syngas 17; syngas 18) subsequent to the syngas effluent (e.g., CPO reactor effluent 15, syngas effluent; syngas 17; syngas 18) exiting the CPO reactor (e.g., CPO reactor 100).

The CPO reactor 100 can be characterized by a CPO pressure (e.g., reactor pressure measured at the reactor exit or outlet) of equal to or greater than about 1 barg, about 10 barg, about 20 barg, about 25 barg, about 30 barn, about 35 barg, about 40 barn, or about 50 barg, alternatively less than about 30 barg, about 25 barg, about 20 barn, or about 10 barg, alternatively from about 1 barg to about 90 barn, alternatively from about 1 barg to about 70 barn, alternatively from about 1 barg to about 40 barn, alternatively from about 1 barg to about 30 barn, alternatively from about 1 barg to about 25 barn, alternatively from about 1 barg to about 20 barg, alternatively from about 1 barg to about 10 barg, alternatively from about 20 barg to about 90 barg, alternatively from about 25 barg to about 85 barg, or alternatively from about 30 barg to about 80 barg.

The CPO reactor 100 can be characterized by a CPO contact time of from about 0.001 milliseconds (ms) to about 5 seconds (s), alternatively from about 0.001 ms to about 1 s, alternatively from about 0.001 ms to about 100 ms, alternatively from about 0.001 ms to about 10 ms, alternatively from about 0.001 ms to about 5 ms, or alternatively from about 0.01 ms to about 1.2 ms. Generally, the contact time of a reactor comprising a catalyst refers to the average amount of time that a compound (e.g., a molecule of that compound) spends in contact with the catalyst (e.g., within the catalyst bed), e.g., the average amount of time that it takes for a compound (e.g., a molecule of that compound) to travel through the catalyst bed. For purposes of the disclosure herein the contact time of less than about 5 ms can be referred to as "millisecond regime" (MSR); and a CPO process or CPO reaction as disclosed herein characterized by a contact time of less than about 5 ms can be referred to as "millisecond regime"—CPO (MSR-CPO) process or reaction, respectively. In some aspects, the CPO reactor 100 can be characterized by a contact time of from about 0.001 ms to about 5 ms, or alternatively from about 0.01 ms to about 1.2 ms.

All of the CPO operational parameters disclosed herein are applicable throughout all of the embodiments disclosed herein, unless otherwise specified. As will be appreciated by one of skill in the art, and with the help of this disclosure, each CPO operational parameter can be adjusted to provide for a desired syngas quality, such as a syngas with a desired composition (e.g., a syngas with a desired $H_2$/CO molar ratio; a syngas with a desired $CO_2$ content; etc.). For example, the CPO operational parameters can be adjusted to provide for an increased $H_2$ content of the syngas. As another example, the CPO operational parameters can be adjusted to provide for a decreased $CO_2$ content of the syngas. As yet another example, the CPO operational parameters can be adjusted to provide for a decreased unreacted hydrocarbons (e.g., unreacted $CH_4$) content of the syngas.

In an aspect, the CPO reactant mixture 10 can further comprise a diluent, such as water and/or steam, $CO_2$, $N_2$, argon, etc. The CPO reactor 100 can be operated under any suitable operational conditions (e.g., CPO operational parameters) that can provide for a CPO reactor effluent (e.g., syngas) with a desired composition (e.g., a desired $H_2$/CO molar ratio; a desired $CO_2$ content; etc.); for example, the CPO reactor 100 can be operated with introducing water and/or steam, and optionally $CO_2$ to the CPO reactor 100.

When carbon is present in the reactor (e.g., coke; C produced as a result of a decomposition reaction as represented by equation (2)), water and/or steam diluent can react with the carbon and generate additional CO and $H_2$, for example as represented by equation (3):

$$C+H_2O \rightleftharpoons CO+H_2 \quad (3)$$

As will be appreciated by one of skill in the art, and with the help of this disclosure, the presence of water and/or steam in the CPO reactor 100 can decrease the amount of coke in the CPO reactor 100.

Further, and as will be appreciated by one of skill in the art, and with the help of this disclosure, water and/or steam can be used to vary the composition of the resulting CPO reactor effluent (e.g., syngas). Steam can react with methane, for example as represented by equation (4):

$$CH_4+H_2O \rightleftharpoons CO+3H_2 \quad (4)$$

In an aspect, a diluent comprising water and/or steam can increase a $H_2$ content of the resulting CPO reactor effluent (e.g., syngas). For example, in aspects where the CPO reactant mixture 10 comprises water and/or steam diluent, the resulting CPO reactor effluent (e.g., syngas) can be characterized by a $H_2$ to CO molar ratio that is increased when compared to a $H_2$ to CO molar ratio of a CPO reactor effluent (e.g., syngas) produced by an otherwise similar process conducted with a reactant mixture comprising hydrocarbons and oxygen without the water and/or steam diluent. Without wishing to be limited by theory, the reforming reaction (e.g., as represented by equation (4)) is an endothermic reaction. The reforming reaction as represented by equation (4) can remove a portion of the process heat (e.g., heat produced by the exothermic CPO reaction, for example as represented by equation (1)).

In the presence of water and/or steam in the CPO reactor 100, CO can react with the water and/or steam to form $CO_2$ and $H_2$ via a water-gas shift (WGS) reaction, for example as represented by eqn. (5):

$$CO+H_2O \rightleftharpoons CO_2+H_2 \quad (5)$$

While the WGS reaction can increase the $H_2$/CO molar ratio of the syngas produced by the CPO reactor 100, it also produces $CO_2$.

In an aspect, the CPO reactor 100 can be operated at an S/C molar ratio in the CPO reactant mixture 10 of less than about 2.4:1, about 2:1, about 1.5:1, about 1:1, about 0.8:1, 0.5:1, alternatively from about 0.01:1 to less than about 2.4:1, alternatively from about 0.05:1 to about 2:1, alternatively from about 0.1:1 to about 1.5:1, alternatively from about 0.15:1 to about 1:1, or alternatively from about 0.2:1 to about 0.8:1. As will be appreciated by one of skill in the art, and with the help of this disclosure, the steam that is introduced to the CPO reactor for use as a diluent in a CPO reaction as disclosed herein is present in significantly smaller amounts than the amounts of steam utilized in steam reforming (e.g., SMR) processes, and as such, a process for producing syngas as disclosed herein can yield a syngas with lower amounts of $H_2$ when compared to the amounts of $H_2$ in a syngas produced by SMR.

The S/C molar ratio in the CPO reactant mixture 10 can be adjusted based on the desired CPO effluent temperature (e.g., target CPO effluent temperature) in order to increase (e.g., maximize) the $H_2$ content of the CPO reactor effluent (e.g., syngas). As will be appreciated by one of skill in the art, and with the help of this disclosure, the reaction (4) that consumes steam in the CPO reactor is preferable over the water-gas shift (WGS) reaction (5) in the CPO reactor 100, as reaction (4) allows for increasing the $H_2$ content of the CPO reactor effluent (e.g., syngas), as well as the M ratio of the CPO reactor effluent (e.g., syngas), wherein the M ratio is a molar ratio defined as $(H_2-CO_2)/(CO+CO_2)$. Further, and as will be appreciated by one of skill in the art, and with the help of this disclosure, reaction (4) converts water and CO to both $H_2$ and $CO_2$.

In an aspect, the amount of methane that reacts according to reaction (3) in the CPO reactor 100 is less than the amount of methane that reacts according to reaction (1) in the CPO reactor 100. In an aspect, less than about 50 mol %, alternatively less than about 40 mol %, alternatively less than about 30 mol %, alternatively less than about 20 mol %, or alternatively less than about 10 mol % of hydrocarbons (e.g., methane) react with steam in CPO reactor 100.

Without wishing to be limited by theory, the presence of water and/or steam in the CPO reactor 100 changes the flammability of the CPO reactant mixture 10, thereby providing for a wider practical range of C/O molar ratios in the CPO reactant mixture 10. Further, and without wishing to be limited by theory, the presence of water and/or steam in the CPO reactor 100 allows for the use of lower C/O molar ratios in the CPO reactant mixture 10. Furthermore, and without wishing to be limited by theory, the presence of water and/or steam in the CPO reactor 100 allows for operating the CPO reactor 100 at relatively high pressures.

As will be appreciated by one of skill in the art, and with the help of this disclosure, the introduction of water and/or steam in the CPO reactor 100 can lead to increasing the amount of unreacted hydrocarbons in the CPO reactor effluent (e.g., syngas). Further, as will be appreciated by one of skill in the art, and with the help of this disclosure, methanol production processes typically tolerate limited amounts of unreacted hydrocarbons in the syngas.

In some aspects, the CPO reactor effluent (e.g., syngas) can comprise less than about 7.5 mol %, alternatively less than about 5 mol %, or alternatively less than about 2.5 mol % hydrocarbons (e.g., unreacted hydrocarbons, unreacted $CH_4$). In such aspects, the CPO reactor effluent can be produced in a CPO process that employs water and/or steam. In such aspects, the CPO reactor effluent can be used for methanol synthesis.

Further, since oxygen is present in the CPO reactant mixture 10, the carbon present in the reactor (e.g., coke; C produced as a result of a decomposition reaction as represented by equation (2)) can also react with oxygen, for example as represented by equation (6):

$$C+O_2 \rightarrow CO_2 \quad (6)$$

When carbon is present in the reactor (e.g., coke; C produced as a result of a decomposition reaction as represented by equation (2)), $CO_2$ (e.g., introduced to the CPO reactor 100 as part of the CPO reactant mixture 10 and/or produced by the reaction represented by equation (6)) can react with C, for example as represented by eqn. (7):

$$C+CO_2 \rightleftharpoons 2CO \quad (7)$$

thereby decreasing the amount of $CO_2$ in the resulting CPO reactor effluent (e.g., syngas). As will be appreciated by one of skill in the art, and with the help of this disclosure, the presence of $CO_2$ in the CPO reactor 100 can decrease the amount of coke in the CPO reactor 100.

Furthermore, $CO_2$ can react with $CH_4$ in a dry reforming reaction, for example as represented by eqn. (8):

$$CH_4+CO_2 \rightleftharpoons 2CO+2H_2 \quad (8)$$

thereby decreasing the amount of $CO_2$ in the resulting CPO reactor effluent (e.g., syngas). Without wishing to be limited by theory, the dry reforming reaction (e.g., as represented by equation (8)) is an endothermic reaction (e.g., highly endothermic reaction). The dry reforming reaction can remove a portion of the process heat (e.g., heat produced by the exothermic CPO reaction, for example as represented by equation (1)).

In an aspect, a diluent comprising $CO_2$ can increase a CO content of the resulting CPO reactor effluent (e.g., syngas). For example, in aspects where the CPO reactant mixture 10 comprises $CO_2$ diluent, the CPO reactor effluent (e.g., syngas) can be characterized by a $H_2$ to CO molar ratio that is decreased when compared to a $H_2$ to CO molar ratio of a CPO reactor effluent (e.g., syngas) produced by an otherwise similar process conducted with a reactant mixture comprising hydrocarbons and oxygen without the $CO_2$ diluent. Without wishing to be limited by theory, $CO_2$ can react with coke inside the CPO reactor 100 and generate additional CO, for example as represented by equation (7). Further, and without wishing to be limited by theory, $CO_2$ can participate in a dry reforming of methane reaction, thereby generating additional CO and $H_2$, for example as represented by equation (8). Dry reforming of methane is generally accompanied by a reaction between $CO_2$ and $H_2$ which results in the formation of additional CO and water.

The use of $CO_2$ in the CPO reactant mixture 10 can advantageously decrease the amount of hydrocarbons converted to $CO_2$ in the CPO reactor 100, for example via a combustion reaction. Without wishing to be limited by theory, and according to Le Chatelier's Principle, the equilibrium of hydrocarbons dry reforming reaction will be shifted towards consuming $CO_2$ with increasing the amount of $CO_2$ in the reactant mixture, thereby allowing for a higher amount of hydrocarbons to convert to syngas.

As will be appreciated by one of skill in the art, and with the help of this disclosure, a $CO_2$-lean syngas has a higher M ratio than a $CO_2$-rich syngas: the lower the $CO_2$ content of the syngas, the higher the M ratio of the syngas. The $CO_2$ content of the syngas can be adjusted as described in more detail in the U.S. Provisional Patent Application 62/787,574 filed Jan. 2, 2019 and entitled "Hydrogen Enrichment in Syngas Produced via Catalytic Partial Oxidation"; which is incorporated by reference herein in its entirety.

In an aspect, a CPO reactor effluent (e.g., syngas) can be recovered from the CPO reactor 100, wherein the CPO reactor effluent (e.g., syngas comprises $H_2$, CO, water, $CO_2$, and unreacted hydrocarbons (e.g., unreacted first hydrocarbons, unreacted methane, optionally unreacted second hydrocarbons, optionally unreacted $C_{4+}$ hydrocarbons).

According to the configuration of the methanol production system 1000 in FIG. 1, the CPO reactor effluent 15 can comprise $H_2$, CO, $CO_2$, water, and unreacted hydrocarbons (e.g., first hydrocarbons and optionally $C_{4+}$ hydrocarbons). The CPO reactor effluent 15 as disclosed herein can be characterized by a $H_2$/CO molar ratio of greater than about 1.6, alternatively greater than about 1.7, alternatively greater than about 1.8, alternatively greater than about 1.9, or alternatively greater than about 2.0. In some aspects, the CPO reactor effluent 15 as disclosed herein can be characterized by a $H_2$/CO molar ratio of from about 1.6 to about 2.3, alternatively from about 1.7 to about 2.2, or alternatively from about 1.8 to about 2.1. In an aspect, the CPO reactor effluent 15 can be characterized by an M ratio of equal to or greater than about 1.6, alternatively equal to or greater than about 1.7, alternatively equal to or greater than about 1.8, alternatively from about 1.6 to about 2.3, alternatively from about 1.7 to about 2.2, or alternatively from about 1.8 to about 2.2.

According to the configuration of the methanol production system 2000 in FIG. 2, the syngas 17 can comprise $H_2$, CO, $CO_2$, water, and unreacted hydrocarbons (e.g., methane, first hydrocarbons, optionally second hydrocarbons, optionally $C_{4+}$ hydrocarbons). The syngas 17 as disclosed herein can be characterized by a $H_2$/CO molar ratio of greater than about 1.7, alternatively greater than about 1.8, alternatively greater than about 1.9, alternatively greater than about 2.0, or alternatively greater than about 2.1. In an aspect, the syngas 17 can be characterized by an M ratio of equal to or greater than about 1.7, alternatively equal to or greater than about 2.0, alternatively equal to or greater than about 2.1, alternatively from about 1.7 to about 2.4, alternatively from about 1.8 to about 2.2, or alternatively from about 1.9 to about 2.1.

According to the configuration of the methanol production system 3000 in FIG. 3, the syngas 18 can comprise $H_2$, CO, $CO_2$, water, and unreacted hydrocarbons (e.g., first hydrocarbons, optionally methane, optionally second hydrocarbons, optionally $C_{4+}$ hydrocarbons). The syngas 18 as disclosed herein can be characterized by a $H_2$/CO molar ratio of greater than about 1.7, alternatively greater than about 1.8, alternatively greater than about 1.9, alternatively greater than about 2.0, or alternatively greater than about 2.1. In an aspect, the syngas 18 can be characterized by an M ratio of equal to or greater than about 1.7, alternatively equal to or greater than about 2.0, alternatively equal to or greater than about 2.1, alternatively from about 1.7 to about 2.4, alternatively from about 1.8 to about 2.2, or alternatively from about 1.9 to about 2.1.

In some aspects, the CPO reactor effluent and/or syngas (e.g., CPO reactor effluent 15, syngas 17, syngas 18) can be used in a downstream process (e.g., methanol production) without further processing to enrich the $H_2$ content of the CPO reactor effluent and/or syngas, respectively.

In other aspects, the CPO reactor effluent and/or syngas (e.g., CPO reactor effluent 15, syngas 17, syngas 18) can be further processed prior to using the CPO reactor effluent and/or syngas (e.g., CPO reactor effluent 15, syngas 17, syngas 18) in a downstream process, such as methanol production. The CPO reactor effluent and/or syngas (e.g., CPO reactor effluent 15, syngas 17, syngas 18) can be processed to enrich its $H_2$ content; for example by contacting the CPO reactor effluent and/or syngas (e.g., CPO reactor effluent 15, syngas 17, syngas 18) with additional (e.g., supplemental) $H_2$ (e.g., hydrogen stream 51; hydrogen-rich stream 70; hydrogen-enriched stream 75).

As will be appreciated by one of skill in the art, and with the help of this disclosure, although the CPO reactor effluent and/or syngas (e.g., CPO reactor effluent 15, syngas 17, syngas 18) can be characterized by a $H_2$/CO molar ratio of greater than about 1.8, which can be appropriate for methanol synthesis, the CPO reactor effluent and/or syngas (e.g., CPO reactor effluent 15, syngas 17, syngas 18) can be processed to further increase its $H_2$ content. Further, as will be appreciated by one of skill in the art, and with the help of this disclosure, the CPO reactor effluent and/or syngas (e.g., CPO reactor effluent 15, syngas 17, syngas 18) can be subjected to minimal processing, such as the recovery of unreacted hydrocarbons, diluent, water, etc., without substantially changing the $H_2$/CO molar ratio of the CPO reactor effluent and/or syngas (e.g., CPO reactor effluent 15, syngas 17, syngas 18). For example, water can be condensed and separated from the CPO reactor effluent and/or syngas (e.g., CPO reactor effluent 15, syngas 17, syngas 18), e.g., in a condenser.

In an aspect, a process as disclosed herein can further comprise (i) recovering at least a portion of the unreacted hydrocarbons (e.g., unreacted first hydrocarbons, optionally unreacted methane, optionally unreacted second hydrocarbons, optionally unreacted $C_{4+}$ hydrocarbons) from the CPO reactor effluent and/or syngas (e.g., CPO reactor effluent 15, syngas 17, syngas 18) to yield recovered hydrocarbons, and (ii) recycling at least a portion of the recovered hydrocarbons to the CPO reactor 100. As will be appreciated by one of skill in the art, and with the help of this disclosure, although fairly high conversions can be achieved in CPO processes (e.g., conversions of equal to or greater than about 90%), the unconverted hydrocarbons could be recovered and recycled back to the CPO reactor 100. In some aspects, at least a portion of the recovered hydrocarbons can be used as fuel (e.g., to preheat the CPO reactant mixture; to heat the cracking reactor) and/or fed to the cracking unit 600.

In an aspect, the CPO reactor effluent and/or syngas (e.g., CPO reactor effluent 15, syngas 17, syngas 18) can have a $CO_2$ content of less than about 7 mol %, alternatively less than about 6 mol %, alternatively less than about 5 mol %, alternatively less than about 4 mol %, alternatively less than about 3 mol %, alternatively less than about 2 mol %, alternatively less than about 1 mol %, alternatively from about 0.1 mol % to about 7 mol %, alternatively from about 0.25 mol % to about 5 mol %, or alternatively from about 0.5 mol % to about 3 mol %. For example, side reactions as represented by equations (7) and/or (8) could lead to a CPO reactor effluent and/or syngas (e.g., CPO reactor effluent 15, syngas 17, syngas 18) that has a $CO_2$ content of from about 0.1 mol % to about 7 mol %.

In an aspect, the CPO reactor effluent and/or syngas (e.g., CPO reactor effluent 15, syngas 17, syngas 18) can have a hydrocarbon content of less than about 10 mol %, alternatively less than about 7.5 mol %, alternatively less than about 5 mol %, alternatively less than about 4 mol %, alternatively less than about 3 mol %, alternatively less than about 2 mol %, alternatively less than about 1 mol %, alternatively less than about 0.1 mol %, or alternatively less than about 0.01 mol %.

In some aspects, for example as illustrated in FIGS. 1 and 3, a process as disclosed herein can comprise a step of feeding a cracking unit feed 60 to a cracking unit 600 to produce a cracking unit product stream 65, a hydrogen-rich stream 70, and a hydrocarbon recovery stream 71. In other aspects, for example as illustrated in FIG. 2, a process as disclosed herein can comprise a step of feeding a cracking unit feed 60 to a cracking unit 600 to produce a cracking unit product stream 65, a hydrogen-lean stream 72, and a hydrocarbon recovery stream 71.

In an aspect, the cracking unit 600 comprises a cracking reactor and a separating unit. In some aspects, for example as illustrated in FIGS. 1 and 3, the cracking unit feed 60 can be introduced to the cracking reactor to produce a cracking reactor product stream, wherein at least a portion of the cracking reactor product stream can be introduced to the separating unit to produce the cracking unit product stream 65, the hydrogen-rich stream 70, and the hydrocarbon recovery stream 71. In other aspects, for example as illustrated in FIG. 2, the cracking unit feed 60 can be introduced to the cracking reactor to produce a cracking reactor product stream, wherein at least a portion of the cracking reactor product stream can be introduced to the separating unit to produce the cracking unit product stream 65, the hydrogen-lean stream 72, and the hydrocarbon recovery stream 71.

The cracking unit 600 can comprise any suitable cracking unit configured to convert saturated hydrocarbons (e.g., alkanes) into olefins. For example, the cracking unit 600 can comprise any suitable cracking reactor configured to convert cracking unit feed 60 comprising second hydrocarbons (e.g., saturated hydrocarbons, alkanes) into cracking reactor product stream comprising olefins. Nonlimiting examples of cracking units (e.g., cracking reactors) suitable for use in the present disclosure include a thermal cracking unit (e.g., a thermal cracking reactor), a catalytic cracking unit (e.g., a catalytic cracking reactor), a steam cracking unit (e.g., steam cracking reactor), and the like, or combinations thereof. As will be appreciated by one of skill in the art, and with the help of this disclosure, the thermal cracking processes, catalytic thermal processes, steam cracking processes, and the like, or combinations thereof are known to one of skill in the art.

Without wishing to be limited by theory, cracking refers to the endothermic reaction that converts alkanes into olefins and hydrogen. Generally, and as will be appreciated by one of skill in the art, and with the help of this disclosure, heat (e.g., thermal energy) has to be supplied to the cracking reactor to enable the cracking reaction that produces olefins. In some aspects, at least a portion of the heat that is used by the cracking reactor can be supplied by the CPO reactor 100, as disclosed herein. As will be appreciated by one of skill in the art, and with the help of this disclosure, the process heat from the CPO reactor 100 may not be enough to supply all heat necessary for the cracking reactor. In an aspect, a fuel stream can be combusted to supply additional heat necessary for the cracking reactor.

In some aspects, the cracking reactor can comprise a gas cracker (e.g., gas cracking reactor). For example, in aspects where the cracking unit feed 60 comprises ethane and/or propane, the cracking reactor can comprise a gas cracker.

In other aspects, the cracking reactor can comprise a liquid cracker (e.g., liquid cracking reactor). For example, in aspects where the cracking unit feed 60 comprises $C_{4+}$ hydrocarbons, such as butanes, naphtha fractions (e.g., naphtha feedstocks), and the like, or combinations thereof; the cracking reactor can comprise a liquid cracker.

In an aspect, the second hydrocarbons suitable for feeding to a cracking unit as disclosed herein can comprise saturated hydrocarbons, such as alkanes. Nonlimiting examples of second hydrocarbons suitable for feeding to a cracking unit as disclosed herein can include alkanes, ethane, propane, butanes, naphtha, and the like, or combinations thereof. In some aspects, the first hydrocarbons and the second hydrocarbons can be the same. For example, a naphtha feed can be introduced to a cracking reactor, as well as to a CPO reactor. In other aspects, the first hydrocarbons and the second hydrocarbons can be different. As another example, ethane (e.g., second hydrocarbons) can be introduced to a cracking reactor and methane (e.g., first hydrocarbons) can be introduced to a CPO reactor.

In some aspects, the separating unit of the cracking unit 600 can comprise any suitable separating unit that is configured to separate the cracking reactor product stream into the cracking unit product stream 65, the hydrogen-rich stream 70, and the hydrocarbon recovery stream 71. In other aspects, the separating unit of the cracking unit 600 can comprise any suitable separating unit that is configured to separate the cracking reactor product stream into the cracking unit product stream 65, the hydrogen-lean stream 72, and the hydrocarbon recovery stream 71.

The cracking reactor product stream comprises olefins (e.g., ethylene, as well as propene, butenes, etc.), $H_2$, methane, and unreacted second hydrocarbons (e.g., alkanes, ethane, propane, butanes, naphtha, and the like, or combinations thereof). For example, the separating unit of the cracking unit 600 can employ gas-liquid separation, distillation, cryogenic distillation, extractive distillation, selective adsorption, selective absorption, and the like, or combinations thereof. The separating unit of the cracking unit 600 can comprise a gas-liquid separator, a distillation column, a cryogenic distillation column, a trayed and/or packed separation column, a compressor, a heat exchanger, a cooling tower, a pressure swing adsorption (PSA) unit, etc.

The separating unit of the cracking unit 600 can comprise a gas-liquid separator. In an aspect, the cracking reactor product stream can be introduced to a gas-liquid separator to produce a hydrocarbon recovery stream (e.g., hydrocarbon recovery stream 71) and a first gas stream. The gas-liquid separator of the cracking unit 600 can comprise any suitable gas-liquid separator configured to separate the cracking reactor product stream into a liquid stream (e.g., hydrocarbon recovery stream, such as hydrocarbon recovery stream 71) and a first gas stream. For example, the gas-liquid separator of the cracking unit 600 can comprise a vapor-liquid separator, flash drum, knock-out drum, knock-out pot, compressor suction drum, etc. The liquid stream can be recovered from the gas-liquid separator of the cracking unit 600 as a bottoms stream. The liquid stream recovered from the gas-liquid separator of the cracking unit 600 can comprise $C_{4+}$ hydrocarbons, such as butanes, butenes, butadiene, pentane, pentenes, hexanes, hexenes, benzene, toluene, xylene, and the like, or combinations thereof. The first gas stream can be recovered from the gas-liquid separator of the cracking unit 600 as an overhead stream. The first gas stream recovered from the gas-liquid separator of the cracking unit 600 can comprise $H_2$, methane, ethane, ethylene, propane, propylene, $CO_2$, CO, and the like, or combinations thereof. As will be appreciated by one of skill in the art, and with the help of this disclosure, the composition of the cracking reactor product stream, the composition of the liquid stream, and the composition of the first gas stream are all dependent on a variety of factors, such as the composition of the cracking unit feed 60, the type of cracker, the operating conditions for the cracker, etc.

In some aspects, at least a portion of the olefins and/or aromatic hydrocarbons can be recovered from the liquid stream to yield olefins and/or aromatic hydrocarbons, respectively, and the hydrocarbon recovery stream 71. In an aspect, at least a portion 71a of the hydrocarbon recovery stream 71 can be fed to the CPO reactor 100. In an aspect, at least a portion of the hydrocarbon recovery stream 71 can be used as fuel (e.g., to preheat the CPO reactant mixture; to heat the cracking reactor) and/or fed to the cracking unit 600.

In an aspect, the first gas stream can be further subjected to one or more separation steps to recover the olefins (e.g., cracking unit product stream 65). In an aspect, the first gas stream can be separated into a second gas stream and the cracking unit product stream 65, for example by employing any suitable separation technique, such as distillation, cryogenic distillation, extractive distillation, selective adsorption, selective absorption, and the like, or combinations thereof. Cracking unit product stream 65 can comprise olefins, such as ethylene and/or propylene. In an aspect, the second gas stream can comprise $H_2$, $CH_4$, ethane, propane, $CO_2$, CO, and the like, or combinations thereof.

In some aspects, the cracking unit product stream 65 can comprise olefins, such as ethylene, propene, butenes, and the like, or combinations thereof. For example, the cracking unit product stream 65 can comprise olefins that have been recovered from the first gas stream. In other aspects, the cracking unit product stream 65 can further comprise other unsaturated hydrocarbons, such as butadiene, $C_{5+}$ olefins, aromatic hydrocarbons, etc. For example, the cracking unit product stream 65 can comprise olefins and other unsaturated hydrocarbons that have been recovered from the liquid stream. The cracking unit product stream 65 can be further subjected to further purification or separation processes, for example for the recovery of one or more components. For example, ethylene can be recovered from the cracking unit product stream 65, wherein ethylene can be further used in a polymerization process.

In aspects where the cracking reactor comprises a gas cracker, such as an ethane cracker and/or a propane cracker, the second gas stream can comprise fairly large amounts of $H_2$ (e.g., from about 5 wt. % to about 65 wt. %, alternatively from about 15 wt. % to about 60 wt. %, or alternatively from about 25 wt. % to about 55 wt. % $H_2$, based on the total weight of the second gas stream), and the second gas stream can be referred to as "hydrogen-rich stream" for purposes of the disclosure herein (e.g., hydrogen-rich stream 70). The hydrogen-rich stream (e.g., hydrogen-rich stream 70) can comprise fairly low amounts of hydrocarbons, such as methane, unreacted hydrocarbons (e.g., ethane, propane), or combinations thereof. For example, the hydrogen-rich stream (e.g., hydrogen-rich stream 70) can comprise from about 35 wt. % to about 95 wt. %, alternatively from about 40 wt. % to about 85 wt. %, or alternatively from about 45 wt. % to about 75 wt. % hydrocarbons (e.g., methane, and optionally ethane and/or propane), based on the total weight of the hydrogen-rich stream (e.g., hydrogen-rich stream 70).

In aspects where the cracking reactor comprises a liquid cracker, such as a naphtha cracker, the second gas stream can comprise fairly low amounts of $H_2$ (e.g., from about 0.1 wt. % to about 25 wt. %, alternatively from about 0.5 wt. % to about 15 wt. %, or alternatively from about 1 wt % to about 10 wt. % $H_2$, based on the total weight of the second gas stream), and the second gas stream can be referred to as "hydrogen-lean stream" for purposes of the disclosure herein (e.g., hydrogen-lean stream 72). The hydrogen-lean stream (e.g., hydrogen-lean stream 72) can comprise fairly large amounts of hydrocarbons, such as methane, unreacted hydrocarbons (e.g., ethane, propane), or combinations thereof. For example, the hydrogen-lean stream (e.g., hydrogen-lean stream 72) can comprise from about 75 wt. % to about 99.9 wt. %, alternatively from about 85 wt. % to about 99.5 wt. %, or alternatively from about 90 wt % to about 99 wt. % hydrocarbons (e.g., methane, and optionally ethane and/or propane), based on the total weight of the hydrogen-lean stream (e.g., hydrogen-lean stream 72).

In an aspect, at least a portion of the hydrogen-lean stream 72 can be fed to the CPO reactor 100. In an aspect, at least a portion of the hydrogen-lean stream 72 can be used as fuel (e.g., to preheat the CPO reactant mixture; to heat the cracking reactor) and/or fed to the cracking unit 600.

While the present disclosure is discussed in detail in the context of a hydrogen-lean stream recovered from a cracking unit being introduced to a CPO reactor, it should be understood that any suitable hydrogen-lean stream can be introduced to the CPO reactor, wherein such hydrogen-lean stream comprises fairly low amounts of $H_2$ (e.g., from about 0.1 wt. % to about 25 wt. %, alternatively from about 0.5 wt. % to about 15 wt. %, or alternatively from about 1 wt. % to about 10 wt. % $H_2$, based on the total weight of the hydrogen-lean stream), as well as fairly large amounts of hydrocarbons (e.g., from about 75 wt. % to about 99.9 wt. %, alternatively from about 85 wt. % to about 99.5 wt. %, or alternatively from about 90 wt. % to about 99 wt. % hydrocarbons, based on the total weight of the hydrogen-lean stream). For example, the hydrogen-lean stream can comprise s a gas stream from a cracking unit, a gas stream from a refinery, a fuel gas stream, fuel gas from fuel gas header, or combinations thereof.

In an aspect, for example as illustrated in FIG. 1, at least a portion 70b of the hydrogen-rich stream 70 can be introduced to a second hydrogen recovery unit 700 (e.g., a PSA unit, a membrane separation unit, a cryogenic separation unit, and the like, or combinations thereof) to further enrich the $H_2$ content of the hydrogen-rich stream 70; e.g., to recover the $H_2$ from the hydrogen-rich stream 70.

In an aspect, for example as illustrated in FIGS. 1 and 3, at least a portion 70c of the hydrogen-rich stream 70 can be introduced to a first hydrogen recovery unit 500 (e.g., a PSA unit, a membrane separation unit, a cryogenic separation unit, and the like, or combinations thereof) to further enrich the $H_2$ content of the hydrogen-rich stream 70; e.g., to recover the $H_2$ from the hydrogen-rich stream 70. In such aspect, the hydrogen-rich stream 70 can be compressed prior to introducing to the first hydrogen recovery unit 500. As will be appreciated by one of skill in the art, and with the help of this disclosure, methanol production loops operate at fairly elevated pressures (e.g. about 70 barg-100 barg), and as such streams (e.g., at least a portion 70c of the hydrogen-rich stream 70) that are introduced to a methanol reaction loop have to compressed to meet the pressure requirements of the methanol production loop.

In some aspects, the first hydrogen recovery unit 500 and the second hydrogen recovery unit 700 can be the same hydrogen recovery unit. In other aspects, the first hydrogen recovery unit 500 and the second hydrogen recovery unit 700 can be different hydrogen recovery units.

In some aspects, at least a portion 70b of the hydrogen-rich stream 70 can be separated into a hydrogen-enriched stream 75 and a hydrocarbon-enriched stream 76 in the second hydrogen recovery unit 700. The hydrogen-enriched stream 75 comprises at least a portion of the $H_2$ of the hydrogen-rich stream 70, and optionally hydrocarbons (e.g., hydrocarbons that were present in the hydrogen-rich stream 70, such as methane, and optionally ethane and/or propane). The hydrocarbon-enriched stream 76 comprises at least a portion of the hydrocarbons (e.g., methane, and optionally ethane and/or propane) of the hydrogen-rich stream 70, and optionally hydrogen. In an aspect, the amount of $H_2$ in the hydrogen-enriched stream 75 is greater than the amount of $H_2$ in the hydrogen-rich stream 70. In an aspect, the amount of hydrocarbons in the hydrocarbon-enriched stream 76 is greater than the amount of hydrocarbons in the hydrogen-rich stream 70.

In an aspect, at least a portion 76a of the hydrocarbon-enriched stream 76 can be fed to the CPO reactor 100. In an aspect, at least a portion of the hydrocarbon-enriched stream 76 can be used as fuel (e.g., to preheat the CPO reactant mixture; to heat the cracking reactor) and/or fed to the cracking unit 600.

In some aspects, at least a portion 71a of the hydrocarbon recovery stream 71 and/or at least a portion of the hydrogen-rich stream 70 can be fed to the CPO reactor 100, for example via the CPO reactant mixture 10. The hydrocarbon recovery stream 71 and/or the hydrogen-rich stream 70 can provide for additional (e.g., supplemental) hydrocarbons to undergo a CPO reaction in the CPO reactor 100.

In other aspects, for example as illustrated in FIG. 2, at least a portion 71a of the hydrocarbon recovery stream 71 and/or at least a portion of the hydrogen-lean stream 72 can be fed to the CPO reactor 100, for example via the CPO reactant mixture 10. The hydrocarbon recovery stream 71 and/or the hydrogen-lean stream 72 can provide for additional (e.g., supplemental) hydrocarbons to undergo a CPO reaction in the CPO reactor 100.

In yet other aspects, for example as illustrated in FIG. 3, at least a portion 71a of hydrocarbon recovery stream 71 and/or at least a portion 76a of hydrocarbon-enriched stream 76 can be fed to the CPO reactor 100, for example via CPO reactant mixture 10. The hydrocarbon recovery stream 71 and/or the hydrocarbon-enriched stream 76 can provide for additional (e.g., supplemental) hydrocarbons to undergo a CPO reaction in the CPO reactor 100.

The $H_2$ present in the CPO reactant mixture 10 (e.g., hydrogen-rich stream 70, hydrogen-lean stream 72, hydrocarbon-enriched stream 76) can combust in the CPO reactor 100 in the presence of oxygen, thereby farther increasing the temperature inside the CPO reactor 100. As will be appreciated by one of skill in the art, and with the help of this disclosure, a controlled increase in the temperature inside the CPO reactor (as opposed to an uncontrolled run-away temperature) can increase the selectivity of the CPO process to CO and $H_2$, thereby providing for a resulting CPO reactor effluent and/or syngas (e.g., CPO reactor effluent 15, syngas 17, syngas 18) with an increased $H_2/CO$ molar ratio (e.g., equal to or greater than about 2.0). The additional process heat generated in the CPO process owing to introducing $H_2$ to the CPO reactor 100 can be further used to heat the cracking reactor, as disclosed herein. However, and as will be appreciated by one of skill in the art, and with the help of this disclosure, the amount of $H_2$ that can be introduced to the CPO reactor 100 is dictated (e.g., controlled) by the ability to control (e.g., regulate) the heat in the CPO reactor, in order to prevent uncontrolled run-away temperatures.

In an aspect, CPO reactant mixture 10 can comprise $H_2$ in an amount of less than about 20 mol %, alternatively less than about 17.5 mol %, alternatively less than about 15 mol %, alternatively less than about 14 mol %, alternatively less than about 12.5 mol %, alternatively less than about 10 mol %, or alternatively less than about 5 mol %.

In an aspect, the hydrogen-rich stream 70 can be fed to the CPO reactor 100 in an amount effective to provide for less than about 20 mol %, or alternatively less than about 14 mol % $H_2$ in CPO reactant mixture 10.

In an aspect, the hydrogen-lean stream 72 can be fed to the CPO reactor 100 in an amount effective to provide for less than about 20 mol %, or alternatively less than about 14 mol % $H_2$ in CPO reactant mixture 10.

In an aspect, the hydrocarbon-enriched stream 76 can be fed to CPO reactor 100 in an amount effective to provide for less than about 20 mol %, or alternatively less than about 14 mol % $H_2$ in the CPO reactant mixture 10.

In aspects where the hydrocarbon recovery stream and/or the hydrogen-rich stream are introduced to the CPO reactor 100, the M ratio and/or the $H_2/CO$ molar ratio of the CPO reactor effluent 15 can be greater than the M ratio and/or the $H_2/CO$ molar ratio, respectively of a syngas produced by an otherwise similar process that feeds a CPO reactant mixture without the hydrocarbon recovery stream and/or without the hydrogen-rich stream to a CPO reactor.

In aspects where the hydrocarbon recovery stream and/or the hydrogen-lean stream are introduced to the CPO reactor 100, the M ratio and/or the $H_2/CO$ molar ratio of the syngas 17 can be greater than the M ratio and/or the $H_2/CO$ molar ratio, respectively of a syngas produced by an otherwise similar process that feeds a CPO reactant mixture without the hydrocarbon recovery stream and/or without the hydrogen-lean stream to a CPO reactor.

In aspects where the hydrocarbon recovery stream and/or hydrocarbon-enriched stream are introduced to the CPO reactor 100, the M ratio and/or the $H_2/CO$ molar ratio of the syngas 18 can be greater than the M ratio and/or the $H_2/CO$ molar ratio, respectively of a syngas produced by an otherwise similar process that feeds a CPO reactant mixture without the hydrocarbon recovery stream and/or without the hydrocarbon-enriched stream to a CPO reactor.

In an aspect, at least a portion of the hydrocarbon recovery stream 71 and/or at least a portion of the hydrocarbon-lean stream 72 can be recycled to the cracking reactor, for example via the cracking unit feed 60. In an aspect, at least a portion of the hydrocarbon recovery stream 71 and/or at least a portion of the hydrocarbon-lean stream 72 can be used as fuel, for example for heating the cracking reactor and/or preheating the CPO reactant mixture.

In an aspect, at least a portion of the hydrocarbon recovery stream 71 and/or at least a portion of the hydrocarbon-enriched stream 76 can be recycled to the cracking reactor, for example via the cracking unit feed 60. In an aspect, at least a portion of the hydrocarbon recovery stream 71 and/or at least a portion of the hydrocarbon-enriched stream 76 can be used as fuel, for example for heating the cracking reactor and/or preheating the CPO reactant mixture.

In an aspect, at least a portion of the hydrogen-rich stream 70 can be contacted with at least a portion of the CPO reactor effluent 15 to produce a hydrogen-enriched syngas 16, for example as illustrated in FIG. 1. The $H_2/CO$ molar ratio of the hydrogen-enriched syngas 16 is greater than the $H_2/CO$ molar ratio of the CPO reactor effluent 15. The M ratio of the hydrogen-enriched syngas 16 is greater than the M ratio of the CPO reactor effluent 15.

In another aspect, at least a portion of the syngas 18 can be contacted with at least a portion of the hydrogen-enriched stream 75 and optionally with at least a portion 70a of the hydrogen-rich stream 70 to produce a hydrogen-enriched syngas 19, for example as illustrated in FIG. 3. The $H_2/CO$ molar ratio of the hydrogen-enriched syngas 19 is greater than the $H_2/CO$ molar ratio of the syngas 18. The M ratio of the hydrogen-enriched syngas 19 is greater than the M ratio of the syngas 18.

The hydrogen-enriched syngas 16, 19 as disclosed herein can be characterized by a $H_2/CO$ molar ratio of greater than about 1.8, alternatively greater than about 1.9, alternatively greater than about 2.0, alternatively greater than about 2.1, or alternatively greater than about 2.2. In an aspect, the hydrogen-enriched syngas 16, 19 as disclosed herein can be characterized by an M ratio of equal to or greater than about 1.8, alternatively equal to or greater than about 2.0, alternatively equal to or greater than about 2.1, alternatively from about 1.8 to about 2.4, alternatively from about 1.9 to about 2.3, or alternatively from about 2.0 to about 2.2.

In an aspect, the hydrogen-enriched syngas 16, 19 as disclosed herein can comprise $CO_2$ in an amount of an amount of less than about 7 mol %, alternatively less than about 6 mol %, alternatively less than about 5 mol %, alternatively less than about 4 mol %, alternatively less than about 3 mol %, alternatively less than about 2 mol %, alternatively less than about 1 mol %, alternatively from about 0.1 mol % to about 7 mol %, alternatively from about 0.25 mol % to about 5 mol %, or alternatively from about 0.5 mol % to about 3 mol %. The amount of $CO_2$ in the hydrogen-enriched syngas 16 can be less than the amount of $CO_2$ in the CPO reactor effluent 15. The amount of $CO_2$ in the hydrogen-enriched syngas 19 can be less than the amount of $CO_2$ in the syngas 18. As will be appreciated by one of skill in the art, and with the help of this disclosure, the hydrogen-containing streams recovered from the cracker unit 600 can have a reduced $CO_2$ content, as compared to an effluent stream from the CPO reactor 100. Consequently, combining hydrogen-containing streams recovered from the cracker unit 600 with an effluent stream from the CPO reactor 100 can result in a stream with a reduced $CO_2$ content as compared to the effluent stream from CPO reactor 100.

In an aspect, the hydrogen-enriched syngas 16, 19 as disclosed herein can comprise hydrocarbons in an amount of an amount of less than about 5 mol %, alternatively less than about 4 mol %, alternatively less than about 3 mol %, alternatively less than about 2 mol %, alternatively less than about 1 mol %, alternatively less than about 0.1 mol %, or alternatively less than about 0.01 mol %. The amount of hydrocarbons in the hydrogen-enriched syngas 16 can be less than the amount of hydrocarbons in the CPO reactor effluent 15. The amount of hydrocarbons in the hydrogen-enriched syngas 19 can be less than the amount of hydrocarbons in the syngas 18. As will be appreciated by one of skill in the art, and with the help of this disclosure, the hydrogen-containing streams recovered from the cracker unit 600 can have a reduced hydrocarbons content, as compared to an effluent stream from the CPO reactor 100. Consequently, combining hydrogen-containing streams recovered from the cracker unit 600 with an effluent stream from the CPO reactor 100 can result in a stream with a reduced hydrocarbons content as compared to the effluent stream from the CPO reactor 100.

In aspects where the syngas (e.g., syngas 17, 18; hydrogen-enriched syngas 16, 19) is characterized by an M ratio of from about 1.8 to about 2.2, the syngas can be further used for methanol ($CH_3OH$) production.

In an aspect, a process for producing methanol as disclosed herein can comprise introducing at least a portion of the syngas (e.g., syngas 17, syngas 18, hydrogen-enriched syngas 16, hydrogen-enriched syngas 19, or combinations thereof) to methanol reactor 200 to produce a methanol reactor effluent stream 30; wherein the methanol reactor effluent stream 30 comprises methanol, water, $H_2$, CO, $CO_2$, and hydrocarbons. The methanol reactor 200 can comprise any reactor suitable for a methanol synthesis reaction from CO and $H_2$, such as for example a trickle bed reactor, a fluidized bed reactor, a slurry reactor, a loop reactor, a cooled multi tubular reactor, and the like, or combinations thereof.

Generally, CO and $H_2$ can be converted into methanol, for example as represented by equation (9):

$$CO+H_2 \rightleftharpoons CH_3OH \quad (9)$$

$CO_2$ and $H_2$ can also be converted to methanol, for example as represented by equation (10):

$$CO_2+3H_2 \rightleftharpoons CH_3OH+H_2O \quad (10)$$

Without wishing to be limited by theory, the lower the $CO_2$ content of the syngas, the lower the amount of water produced in the methanol reactor 200. As will be appreciated by one of skill in the art, and with the help of this disclosure, syngas produced by SMR has a fairly high content of $H_2$ (as compared to the $H_2$ content of syngas produced by CPO), and a syngas with an elevated $H_2$ content can promote the $CO_2$ conversion to methanol, for example as represented by equation (10), which in turn can lead to an increased water content in a crude methanol stream (e.g., crude methanol stream 40).

Methanol synthesis from CO, $CO_2$ and $H_2$ is a catalytic process, and is most often conducted in the presence of copper based catalysts. The methanol reactor 200 can comprise a methanol production catalyst, such as any suitable commercial catalyst used for methanol synthesis. Nonlimiting examples of methanol production catalysts suitable for use in the methanol reactor 200 in the current disclosure include Cu, Cu/ZnO, $Cu/ThO_2$, $Cu/Zn/Al_2O_3$, Cu/ZnO/ $Al_2O_3$. Cu/Zr, and the like, or combinations thereof.

In an aspect, a process for producing methanol as disclosed herein can comprise a step of separating at least a portion of the methanol reactor effluent stream 30 into a crude methanol stream 40 and a vapor stream 50; wherein the crude methanol stream 40 comprises methanol and water; wherein the vapor stream 50 comprises $H_2$, CO, $CO_2$, and hydrocarbons (e.g., first hydrocarbons and/or second hydrocarbons). The methanol reactor effluent stream 30 can be separated into crude methanol stream 40 and vapor stream 50 in the gas-liquid separator 300, such as a vapor-liquid separator, flash drum, knock-out drum, knock-out pot, compressor suction drum, etc.

In an aspect, a process for producing methanol as disclosed herein can comprise a step of separating at least a portion of the crude methanol stream 40 in the distillation unit 400 into a methanol stream 45 and a water stream 46, wherein the distillation unit 400 comprises one or more distillation columns. The water stream 46 comprises water and residual methanol. Generally, the one or more distillation columns can separate components of the crude methanol stream 40 based on their boiling points. As will be appreciated by one of skill in the art, and with the help of this disclosure, the higher the water content of the crude methanol stream 40, the more distillation columns are necessary to purify the methanol.

In an aspect, the methanol stream 45 can comprise methanol in an amount of equal to or greater than about 95 wt. %, alternatively equal to or greater than about 97.5 wt. %, alternatively equal to or greater than about 99 wt. %, or alternatively equal to or greater than about 99.9 wt. %, based on the total weight of the methanol stream 45.

In an aspect, a process for producing methanol as disclosed herein can comprise a step of separating at least a portion of the vapor stream 50 into a hydrogen stream 51 and a residual gas stream 52, wherein the hydrogen stream 51 comprises at least a portion of the $H_2$ of the vapor stream 50, and wherein the residual gas stream 52 comprises CO, $CO_2$, and hydrocarbons (e.g., first hydrocarbons and/or second hydrocarbons). The vapor stream 50 can be separated into the hydrogen stream 51 and the residual gas stream 52 in the first hydrogen recovery unit 500, such as a PSA unit, a membrane separation unit, a cryogenic separation unit, and the like, or combinations thereof. In some aspects, at least a portion 70c of the hydrogen-rich stream 70 can be introduced to the first hydrogen recovery unit 500.

In an aspect, a process for producing methanol as disclosed herein can comprise recycling at least a portion 51a of hydrogen stream 51 to the methanol reactor 200; for example via a syngas feed to methanol reactor 200.

In some aspects, at least a portion of the residual gas stream 52 can be purged. In other aspects, at least a portion of the residual gas stream 52 can be used as fuel, for example for pre-heating the CPO reactant mixture 10, heating the cracking reactor in the cracking unit 600, and the like, or combinations thereof.

In other aspects, at least a portion 52a of the residual gas stream 52 can be fed to the CPO reactor 100. In yet other aspects, at least a portion of the residual gas stream 52 can be fed to the cracking reactor.

In an aspect, a process for producing methanol and olefins as disclosed herein can comprise the steps of (a) feeding a cracking unit feed 60 to a cracking unit 600 to produce a cracking unit product stream 65, a hydrogen-rich stream 70, and a hydrocarbon recovery stream 71; wherein the cracking unit feed 60 comprises second hydrocarbons; wherein the cracking unit product stream 65 comprises olefins; wherein the hydrogen-rich stream 70 comprises $H_2$, methane, and optionally unreacted second hydrocarbons; and wherein the hydrocarbon recovery stream 71 comprises $C_{4+}$ hydrocarbons; (b) introducing at least a portion 70b of the hydrogen-rich stream 70 to a second hydrogen recovery unit 700 to produce a hydrogen-enriched stream 75 and a hydrocarbon-enriched stream 76; wherein the hydrogen-enriched stream 75 comprises at least a portion of the $H_2$ of the hydrogen-rich stream 70; and wherein the hydrocarbon-enriched stream 76 comprises at least a portion of the hydrocarbons of the hydrogen-rich stream 70; (c) feeding a catalytic partial oxidation (CPO) reactant mixture 10 to a CPO reactor 100; wherein the CPO reactant mixture 10 comprises oxygen, first hydrocarbons, optionally at least a portion 71a of the hydrocarbon recovery stream 71 and/or at least a portion 76a of the hydrocarbon-enriched stream 76, and optionally steam; wherein the first hydrocarbons and the second hydrocarbons are the same or different; wherein at least a portion of the hydrocarbons in the CPO reactant mixture react, via a CPO reaction, in the CPO reactor 100 to produce a syngas 18; wherein the hydrocarbons in the CPO reactant mixture comprise first hydrocarbons, optionally methane, optionally second hydrocarbons, and optionally $C_{4+}$ hydrocarbons; wherein the CPO reactor 100 comprises a CPO catalyst; wherein the syngas 18 comprises $H_2$, CO, $CO_2$, water, and unreacted hydrocarbons, wherein the syngas 18 is characterized by an M ratio of the syngas 18, wherein the M ratio is a molar ratio defined as $(H_2-CO_2)/(CO+CO_2)$; and wherein the syngas 18 is characterized by a $H_2$ to $CO(H_2/CO)$ molar ratio of the syngas 18; (d) contacting at least a portion of the syngas 18 with at least a portion of the hydrogen-enriched stream 75 to yield a hydrogen-enriched syngas 19; wherein the hydrogen-enriched syngas 19 is characterized by an M ratio of the hydrogen-enriched syngas 19, wherein the M ratio of the hydrogen-enriched syngas 19 is greater than the M ratio of the syngas 18; wherein the hydrogen-enriched syngas 19 is characterized by a $H_2/CO$ molar ratio of the hydrogen-enriched syngas 19, and wherein the $H_2/CO$ molar ratio of the hydrogen-enriched syngas 19 is greater than the $H_2/CO$ molar ratio of the syngas 18; (e) introducing at least a portion of the hydrogen-enriched syngas 19 to a methanol reactor 200 to produce a methanol reactor effluent stream 30; wherein the methanol reactor effluent stream 30 comprises methanol, water, $H_2$, CO, $CO_2$, methane, first hydrocarbons, and optionally second hydrocarbons and/or $C_{4+}$ hydrocarbons; (f) separating at least a portion of the methanol reactor effluent stream 30 into a crude methanol stream 40 and a vapor stream 50; wherein the crude methanol stream 40 comprises methanol and water; and wherein the vapor stream 50 comprises $H_2$, CO, $CO_2$, methane, first hydrocarbons, and optionally second hydrocarbons and/or $C_{4+}$ hydrocarbons; (g) introducing at least a portion of the vapor stream 50 to a first hydrogen recovery unit 500 to produce a hydrogen stream 51 and a residual gas stream 52, wherein the hydrogen stream 51 comprises at least a portion of the $H_2$ of the vapor stream 50, and wherein the residual gas stream 52 comprises CO, $CO_2$, methane, first hydrocarbons, and optionally second hydrocarbons and/or $C_{4+}$ hydrocarbons; (h) recycling at least a portion 51a of the hydrogen stream 51 to the methanol reactor 200; (i) optionally recycling at least a portion 52a of the residual gas stream 52 to the CPO reactor 100; (j) separating at least a portion of the crude methanol stream 40 into a methanol stream 45 and a water stream 46 in a distillation unit 400; and (k) optionally cooling 13 the CPO reactor 100; wherein cooling 13 the CPO reactor 100 comprises heating 13' the cracking unit 600 while cooling 13 the CPO reactor 100 by heat transfer between the CPO reactor 100 and the cracking unit 600. In such aspect, the M ratio of the hydrogen-enriched syngas 19 can be equal to or greater than about 1.8, and the $H_2/CO$ molar ratio of the hydrogen-enriched syngas 19 can be greater than about 2.0. In such aspect, the second hydrocarbons can comprise ethane, wherein the cracking unit 600 can comprises an ethane cracker, and wherein the olefins comprise ethylene.

In an aspect, a process as disclosed herein can comprise setting up a modular system for the production of olefins and methanol, wherein the modular system can comprise a cracking unit (e.g. cracking unit 600); a CPO unit (e.g., CPO reactor 100); and a methanol production unit. Each unit of the modular system can be mounted on a movable platform (e.g., skid) and transported and placed at an oil or gas well site to produce olefins and methanol. Each unit of the modular system mounted on a movable platform can be advantageously transported to remote locations, for example a remote location with gas producing well heads (e.g., well head for the production of natural gas and/or associated gas, etc.). A portion of the gas hydrocarbons in the remote location can be converted into syngas, followed by methanol synthesis, and as such liquid methanol would be advantageously transported from the remote location (as opposed to natural gas, associated gas, etc.). Liquid pipelines are generally more advantageous when compared to gas pipelines. In some aspects, the produced olefins could be compressed, stored, transported, etc.

In an embodiment, setting up at least one modular system for processing stranded remote gas at a wellbore site can comprise transporting each unit of the modular system to the wellbore site, wherein each unit can be transported concurrently, sequentially, or combinations thereof, with respect to the other units. Accordingly, each unit will be sized and configured for ease of transport to the wellsite. For example, a unit for service at terrestrial sites may be sized and configured for overland transport (e.g., placed on a trailer or skid) as a standard or oversize tractor-trailer transport A unit for service at offshore sites may be sized and configured for ship transport (e.g., placed on a barge or skid). Each unit can be optionally stored at the wellbore site, as necessary. Each unit can be placed and/or positioned at the wellsite in a cooperative structural arrangement or position (including at various elevations, if needed for example to facilitate gravity flow).

In an aspect, a process for producing syngas and olefins as disclosed herein can advantageously display improvements in one or more process characteristics when compared to an otherwise similar process that does not integrate a CPO reactor with a cracking unit. The process as disclosed herein can advantageously utilize hydrocarbon-rich cracker off-gas as a feed to the CPO reactor, as well as hydrogen-rich cracker off-gas to increase the $H_2$ content of a CPO reactor effluent. As will be appreciated by one of skill in the art, and with the help of this disclosure, since the CPO reaction is exothermic, very little heat supply in the form of fuel combustion is needed (e.g., for pre-heating reactants in the reaction mixture that is supplied to a syngas generation section), when compared to conventional steam reforming. As such, the process for producing syngas as disclosed herein can advantageously generate less $CO_2$ through fuel burning, when compared to steam reforming.

Further, the process as disclosed herein can utilize process heat from the CPO reactor to heat a cracking unit, thereby preventing run-away temperatures in the CPO reactor (e.g., in a CPO catalyst bed), which could lead to catalyst deactivation. As will be appreciated by one of skill in the art, and with the help of this disclosure, operating the CPO reactor at a relatively low C/O ratio (e.g., less than about 2:1) can lead to run-away temperatures, and thus removing heat from the CPO reactor can advantageously enable operating the CPO reactor at relatively low C/O ratios.

In an aspect, the hydrogen-rich stream 70 can be advantageously mixed into the CPO reactant mixture 10 such that the resulting CPO reactant mixture 10 has a $H_2$ content of less than about 20 mol %, or alternatively less than about 14 mol %, which allows for the hydrocarbons in the hydrogen-rich stream 70 to be utilized in the CPO reaction. As will be appreciated by one of skill in the art, and with the help of this disclosure, the hydrogen-rich stream 70 is produced when the cracking reactor is an ethane cracker. Further, and as will be appreciated by one of skill in the art, and with the help of this disclosure, cracking of feedstock other than ethane results in a cracker effluent that has low $H_2$ in the off-gas, thereby leading to a hydrogen-lean stream (e.g., hydrogen-lean stream 72). In an aspect, the hydrogen-lean stream 72 can be advantageously mixed into the CPO reactant mixture 10, wherein the resulting CPO reactant mixture 10 has a $H_2$ content of less than about 20 mol %, or alternatively less than about 14 mol %.

In an aspect, the off-gas from ethane cracker (e.g., hydrogen-rich stream 70) has higher $H_2$ content than hydrogen-lean streams produced by cracking feeds other than ethane, and as such the hydrogen-rich stream 70 can be subjected to separation of $H_2$ and unconverted hydrocarbons, which could be accomplished by using an existing hydrogen separation unit (e.g., first $H_2$ recovery unit 500) in the methanol loop, or a separate unit (e.g., second $H_2$ recovery unit 700). The $H_2$ recovered from the hydrogen separation units 500, 700 can be advantageously recycled 51a, 75 to the methanol loop inlet and the unconverted hydrocarbons can be advantageously recycled 52a, 76a to the CPOX reactor 100. As disclosed herein, in aspects where off-gas from ethane cracker (e.g., hydrogen-rich stream 70) is introduced directly (e.g., with no separation, no hydrogen recovery) into the CPO reactor feed (e.g., CPO reactant mixture 10), the resulting CPO reactant mixture 10 can have a $H_2$ content of less than about 20 mol %, or alternatively less than about 14 mol % in the combined feed to CPOX reactor.

In an aspect, a process for producing syngas and olefins as disclosed herein can advantageously comprise introducing at least a portion 70c of the hydrogen-rich stream 70 after compression to the first $H_2$ recovery unit 500 of the methanol loop. In such aspect, a process for producing syngas and olefins as disclosed herein can advantageously comprise introducing at least a portion 52a of the residual as stream 52 from a portion of the purge stream from the first $H_2$ recovery unit 500 to the CPO reactor 100 via the CPO reactant mixture 10. In such aspect, hydrocarbons in the hydrogen-rich stream 70 would accumulate less or would not accumulate in the methanol loop, thereby reducing the size of the methanol loop equipment. In such aspect, hydrocarbons in the hydrogen-rich stream 70 can be advantageously converted to syngas in the CPO reactor 100. In such aspect, the second $H_2$ recovery unit (e.g., second $H_2$ recovery unit 700) can be advantageously eliminated. Additional advantages of the processes for the production of syngas and/or methanol as disclosed herein can be apparent to one of skill in the art viewing this disclosure.

EXAMPLES

The subject matter having been generally described, the following examples are given as particular embodiments of the disclosure and to demonstrate the practice and advantages thereof. It is understood that the examples are given by way of illustration and are not intended to limit the specification of the claims to follow in any manner.

Example 1

The yields from cracking light hydrocarbon feedstocks via a conventional cracking process (e.g. gas cracking process) are displayed in Table 1.

TABLE 1

Representative yields from light hydrocarbon feedstocks

| | Ethane (%) | Propane (%) | Butane (%) |
|---|---|---|---|
| Conversion per pass | 60 | 90 | 95 |
| Once through Yields (wt. %) | | | |
| $CO/CO_2/H_2S$ | 0.20 | 0.2 | 0.4 |
| $H_2$ | 3.5 | 1.5 | 1.0 |
| $CH_4$ | 4.3 | 23.8 | 22.5 |
| $C_2H_2$ | 0.2 | 0.7 | 0.5 |
| $C_2H_4$ | 47.7 | 36.5 | 34.5 |
| $C_2H_6$ | 40.0 | 3.2 | 4.5 |
| $C_3H_4$ | 0.05 | 0.5 | 0.4 |
| $C_3H_6$ | 1.15 | 14.7 | 16.5 |
| $C_3H_8$ | 0.4 | 10.0 | 0.4 |
| $C_4H_6$ | 1.4 | 2.65 | 3.5 |
| $C_4H_8$ | 0.15 | 1.15 | 3.2 |
| $C_4H_{10}$ | 0.25 | n.a | 3.4 |
| $C_{5+}$ | 0.7 | 5.1 | 9.2 |
| TOTAL | 100 | 100 | 100 |
| Ultimate Ethylene yields including recycle flows | 80 | 45.5 | 38.4 |

Additional Disclosure

A first aspect, which is a process for producing syngas and olefins comprising (a) feeding a catalytic partial oxidation (CPO) reactant mixture to a CPO reactor; wherein the CPO reactant mixture comprises oxygen, first hydrocarbons, and optionally steam; wherein at least a portion of the CPO reactant mixture reacts, via a CPO reaction, in the CPO reactor to produce a CPO reactor effluent; wherein the CPO reactor comprises a CPO catalyst; wherein the CPO reactor effluent comprises hydrogen ($H_2$), carbon monoxide (CO), carbon dioxide ($CO_2$), water, and unreacted first hydrocarbons, and wherein the CPO reactor effluent is characterized by an M ratio of the CPO reactor effluent, wherein the M ratio is a molar ratio defined as $(H_2-CO_2)/(CO+CO_2)$; (b) feeding a cracking unit feed to a cracking unit to produce a cracking unit product stream, a hydrogen-rich stream, and a hydrocarbon recovery stream; wherein the cracking unit feed comprises second hydrocarbons; wherein the first hydrocarbons and the second hydrocarbons are the same or different; wherein the cracking unit product stream comprises olefins; wherein the hydrogen-rich stream comprises $H_2$, methane, and optionally unreacted second hydrocarbons; and wherein the hydrocarbon recovery stream comprises $C_{4+}$ hydrocarbons; and (c) contacting at least a portion of the CPO reactor effluent with at least a portion of the hydrogen-rich stream to yield hydrogen-enriched syngas, wherein the hydrogen-enriched syngas is characterized by an M ratio of the hydrogen-enriched syngas, and wherein the M ratio of the hydrogen-enriched syngas is greater than the M ratio of the CPO reactor effluent. A second aspect, which is the process of the first aspect, wherein the first hydrocarbons and/or the second hydrocarbons comprise methane, ethane, propane, butanes, naptha, natural gas, natural gas liquids, associated gas, well head gas, enriched gas, paraffins, shale gas, shale liquids, fluid catalytic cracking (FCC) off gas, refinery process gases, stack gases, fuel gas from fuel gas header, or combinations thereof; and wherein the olefins comprise ethylene. A third aspect, which is the process of any one of the first and the second aspects, wherein the hydrogen-enriched syngas comprises carbon dioxide in an amount of from about 0.25 mol % to about 5 mol %. A fourth aspect, which is the process of any one of the first through the third aspects, wherein the cracking unit comprises a cracking reactor and a separating unit; and wherein the process further comprises cooling the CPO reactor; wherein cooling the CPO reactor comprises heating the cracking reactor while cooling the CPO reactor by heat transfer between the CPO reactor and the cracking reactor. A fifth aspect, which is the process of any one of the first through the fourth aspects, wherein the CPO reactor is characterized by at least one CPO operational parameter selected from the group consisting of a CPO feed temperature of from about 25° C. to about 600° C.; a CPO effluent temperature of from about 300° C. to about 1,600° C.; a CPO pressure of from about 1 barn to about 90 barg; a CPO contact time of from about 0.001 milliseconds (ms) to about 5 seconds (s); a carbon to oxygen (C/O) molar ratio in the CPO reactant mixture of from about 0.5:1 to about 3:1, wherein the C/O molar ratio refers to the total moles of carbon (C) of hydrocarbons in the reactant mixture divided by the total moles of oxygen ($O_2$) in the reactant mixture; a steam to carbon (S/C) molar ratio in the CPO reactant mixture of from about 0.01:1 to less than about 2.4:1, wherein the S/C molar ratio refers to the total moles of water ($H_2O$) in the reactant mixture divided by the total moles of carbon (C) of hydrocarbons in the reactant mixture; and combinations thereof. A sixth aspect, which is the process of any one of the first through the fifth aspects, wherein the M ratio of the hydrogen-enriched syngas is equal to or greater than about 1.8. A seventh aspect, which is the process of any one of the first through the sixth aspects, wherein the hydrogen-enriched syngas is characterized by a hydrogen to carbon monoxide ($H_2/CO$) molar ratio of greater than about 2.0; and wherein the $H_2/CO$ molar ratio of the hydrogen-enriched syngas is greater than the $H_2/CO$ molar ratio of the CPO reactor effluent. An eighth aspect, which is the process of any one of the first through the seventh aspects further comprising (i) introducing at least a portion of the hydrogen-enriched syngas to a methanol reactor to produce a methanol reactor effluent stream; wherein the methanol reactor effluent stream comprises methanol, water, $H_2$, CO, $CO_2$, methane, first hydrocarbons, and optionally second hydrocarbons; (ii) separating at least a portion of the methanol reactor effluent stream into a crude methanol stream and a vapor stream; wherein the crude methanol stream comprises methanol and water; and wherein the vapor stream comprises $H_2$, CO, $CO_2$, methane, first hydrocarbons, and optionally second hydrocarbons; (iii) introducing at least a portion of the vapor stream to a first hydrogen recovery unit to produce a hydrogen stream and a residual gas stream, wherein the hydrogen stream comprises at least a portion of the hydrogen of the vapor stream, and wherein the residual gas stream comprises CO, $CO_2$, methane, first hydrocarbons, and optionally second hydrocarbons; (iv) recycling at least a portion of the hydrogen stream to the methanol reactor; and (v) separating at least a portion of the crude methanol stream into a methanol stream and a water stream. A ninth aspect, which is the process of the eighth aspect, wherein (1) at least a portion of the residual gas stream is purged, used as fuel, fed to the CPO reactor in step (a), or combinations thereof; and/or (2) at least a portion of the hydrocarbon recovery stream is recycled to the cracking unit, used as fuel, fed to the CPO reactor in step (a), or combinations thereof. A tenth aspect, which is a process for producing syngas and olefins comprising (a) feeding a cracking unit feed to a cracking unit to produce a cracking unit product stream, a hydrogen-lean stream, and a hydrocarbon recovery stream; wherein the cracking unit feed comprises second hydrocarbons; wherein the cracking unit product stream comprises olefins; wherein the hydrogen-lean stream comprises $H_2$, methane, and optionally unreacted second hydrocarbons; and wherein the hydrocarbon recovery stream comprises $C_{4+}$ hydrocarbons; and (b) feeding a catalytic partial oxidation (CPO) reactant mixture to a CPO reactor; wherein the CPO reactant mixture comprises oxygen, first hydrocarbons, at least a portion of the hydrogen-lean stream, and optionally steam and/or at least a portion of the hydrocarbon recovery stream; wherein the first hydrocarbons and the second hydrocarbons are the same or different; wherein at least a portion of the hydrocarbons in the CPO reactant mixture react, via a CPO reaction, in the CPO reactor to produce a syngas; wherein the hydrocarbons in the CPO reactant mixture comprise first hydrocarbons, methane, and optionally second hydrocarbons and/or $C_{4+}$ hydrocarbons; wherein the CPO reactor comprises a CPO catalyst; wherein the syngas comprises $H_2$, CO, $CO_2$, water, and unreacted hydrocarbons; wherein the syngas is characterized by an M ratio of the syngas, wherein the M ratio is a molar ratio defined as $(H_2-CO_2)/(CO+CO_2)$; and wherein the syngas is characterized by a hydrogen to carbon monoxide ($H_2/CO$) molar ratio of the syngas. An eleventh aspect, which is the process of the tenth aspect, wherein (1) the M ratio of the syngas is equal to or greater than about 1.8; and/or (2) the $H_2/CO$ molar ratio of the syngas is greater than about 2.0. A twelfth aspect, which is the process of any one of the tenth and eleventh aspects, wherein the CPO reactant mixture comprises hydrogen in an amount of less than about 20 mol %. A thirteenth aspect, which is the process of any one of the tenth though the twelfth aspects, wherein the M ratio and/or the $H_2/CO$ molar ratio of the syngas is greater than the M ratio and/or the $H_2/CO$ molar ratio, respectively of a syngas produced by an otherwise similar process that feeds a CPO reactant mixture without the hydrogen-lean stream to a CPO reactor. A fourteenth aspect, which is the process of any one of the tenth though the twelfth aspects, further comprising (i) introducing at least a portion of the syngas to a methanol reactor to produce a methanol reactor effluent stream; wherein the methanol reactor effluent stream comprises methanol, water, $H_2$, CO, $CO_2$, methane, first hydrocarbons, and optionally second hydrocarbons and/or $C_{4+}$ hydrocarbons; (ii) separating at least a portion of the methanol reactor effluent stream into a crude methanol stream and a vapor stream; wherein the crude methanol stream comprises methanol and water; and wherein the vapor stream comprises $H_2$, CO, $CO_2$, methane, first hydrocarbons, and optionally second hydrocarbons and/or $C_{4+}$ hydrocarbons; (iii) introducing at least a portion of the vapor stream to a first hydrogen recovery unit to produce a hydrogen stream and a residual gas stream, wherein the hydrogen stream comprises at least a portion of the hydrogen of the vapor stream, and wherein the residual gas stream comprises CO, $CO_2$, methane, first hydrocarbons, and optionally second hydrocarbons and/or $C_{4+}$ hydrocarbons; (iv) recycling at least a portion of the hydrogen stream to the methanol reactor; (v) separating at least a portion of the crude methanol stream into a methanol stream and a water stream; and (vi) optionally recycling at least a portion of the residual gas stream to the CPO reactor. A fifteenth aspect, which is a process producing methanol and olefins comprising (a) feeding a cracking unit feed to a cracking unit to produce a cracking unit product stream, a hydrogen-rich stream, and a hydrocarbon recovery stream; wherein the cracking unit feed comprises second hydrocarbons; wherein the cracking unit product stream comprises olefins; wherein the hydrogen-rich stream comprises $H_2$, methane, and optionally unreacted second hydrocarbons; and wherein the hydrocarbon recovery stream comprises $C_{4+}$ hydrocarbons; (b) introducing at least a portion of the hydrogen-rich stream to a second hydrogen recovery unit to produce a hydrogen-enriched stream and a hydrocarbon-enriched stream; wherein the hydrogen-enriched stream comprises at least a portion of the $H_2$ of the hydrogen-rich stream; and wherein the hydrocarbon-enriched stream comprises at least a portion of the hydrocarbons of the hydrogen-rich stream; (c) feeding a catalytic partial oxidation (CPO) reactant mixture to a CPO reactor; wherein the CPO reactant mixture comprises oxygen, first hydrocarbons, optionally at least a portion of the hydrocarbon recovery stream and/or at least a portion of the hydrocarbon-enriched stream, and optionally steam; wherein the first hydrocarbons and the second hydrocarbons are the same or different; wherein at least a portion of the hydrocarbons in the CPO reactant mixture react, via a CPO reaction, in the CPO reactor to produce a syngas; wherein the hydrocarbons in the CPO reactant mixture comprise first hydrocarbons, optionally methane, optionally second hydrocarbons, and optionally $C_{4+}$ hydrocarbons; wherein the CPO reactor comprises a CPO catalyst; wherein the syngas comprises $H_2$, CO, $CO_2$, water, and unreacted hydrocarbons; wherein the syngas is characterized by an M ratio of the syngas, wherein the M ratio is a molar ratio defined as $(H_2-CO_2)/(CO+CO_2)$; and wherein the syngas is characterized by a $H_2$ to CO($H_2/CO$) molar ratio of the syngas; (d) contacting at least a portion of the syngas with at least a portion of the hydrogen-enriched stream to yield hydrogen-enriched syngas; wherein the hydrogen-enriched syngas is characterized by an M ratio of the hydrogen-enriched syngas, wherein the M ratio of the hydrogen-enriched syngas is greater than the M ratio of the syngas; wherein the hydrogen-enriched syngas is characterized by a $H_2/CO$ molar ratio of the hydrogen-enriched syngas, and wherein the $H_2/CO$ molar ratio of the hydrogen-enriched syngas is greater than the $H_2/CO$ molar ratio of the syngas; (e) introducing at least a portion of the hydrogen-enriched syngas to a methanol reactor to produce a methanol reactor effluent stream; wherein the methanol reactor effluent stream comprises methanol, water, $H_2$, CO, $CO_2$, methane, first hydrocarbons, and optionally second hydrocarbons and/or $C_{4+}$ hydrocarbons; (f) separating at least a portion of the methanol reactor effluent stream into a crude methanol stream and a vapor stream; wherein the crude methanol stream comprises methanol and water; and wherein the vapor stream comprises $H_2$, CO, $CO_2$, methane, first hydrocarbons, and optionally second hydrocarbons and/or $C_{4+}$ hydrocarbons; (g) introducing at least a portion of the vapor stream to a first hydrogen recovery unit to produce a hydrogen stream and a residual gas stream, wherein the hydrogen stream comprises at least a portion of the $H_2$ of the vapor stream, and wherein the residual gas stream comprises CO, $CO_2$, methane, first hydrocarbons, and optionally second hydrocarbons and/or $C_{4+}$ hydrocarbons; (h) recycling at least a portion of the hydrogen stream to the methanol reactor; (i) optionally recycling at least a portion of the residual gas stream to the CPO reactor; (j) separating at least a portion of the crude methanol stream into a methanol stream and a water stream; and (k) optionally cooling the CPO reactor; wherein cooling the CPO reactor comprises heating the cracking unit while cooling the CPO reactor by heat transfer between the CPO reactor and the cracking unit A sixteenth aspect, which is the process of the fifteenth aspect, wherein the M ratio of the hydrogen-enriched syngas is equal to or greater than about 1.8, and wherein the $H_2$/CO molar ratio of the hydrogen-enriched syngas is greater than about 2.0. A seventeenth aspect, which is the process of any one of the fifteenth and the sixteenth aspects, wherein each of the first hydrogen recovery unit and the second hydrogen recovery unit can independently comprise a pressure swing adsorption (PSA) unit, a membrane separation unit, a cryogenic separation unit, or combinations thereof. An eighteenth aspect, which is the process of any one of the fifteenth through the seventeenth aspects, wherein the second hydrocarbons comprise ethane, wherein the cracking unit comprises an ethane cracker, and wherein the olefins comprise ethylene. A nineteenth aspect which is a process for producing syngas comprising feeding a catalytic partial oxidation (CPO) reactant mixture to a CPO reactor; wherein the CPO reactant mixture comprises oxygen, first hydrocarbons, at least a portion of a hydrogen-lean stream, and optionally steam; wherein the hydrogen-lean stream comprises $H_2$, methane, and optionally $C_{2-3}$ hydrocarbons; wherein at least a portion of the hydrocarbons in the CPO reactant mixture react, via a CPO reaction, in the CPO reactor to produce a syngas; wherein the hydrocarbons in the CPO reactant mixture comprise first hydrocarbons, methane, and optionally $C_{2-3}$ hydrocarbons; wherein the CPO reactor comprises a CPO catalyst; wherein the syngas comprises $H_2$, CO, $CO_2$, water, and unreacted hydrocarbons; and wherein the CPO reactant mixture comprises $H_2$ in an amount of less than about 15 mol %. A twentieth aspect, which is the process of the nineteenth aspect, wherein the hydrogen-lean stream comprises a gas stream from a cracking unit, a gas stream from a refinery, a fuel gas stream, fuel gas from fuel gas header, or combinations thereof.

For the purpose of any U.S. national stage filing from this application, all publications and patents mentioned in this disclosure are incorporated herein by reference in their entireties, for the purpose of describing and disclosing the constructs and methodologies described in those publications, which might be used in connection with the methods of this disclosure. Any publications and patents discussed herein are provided solely for their disclosure prior to the filing date of the present application. Nothing herein is to be construed as an admission that the inventors are not entitled to antedate such disclosure by virtue of prior invention.

In any application before the United States Patent and Trademark Office, the Abstract of this application is provided for the purpose of satisfying the requirements of 37 C.F.R. § 1.72 and the purpose stated in 37 C.F.R. § 1.72(b) "to enable the United States Patent and Trademark Office and the public generally to determine quickly from a cursory inspection the nature and gist of the technical disclosure." Therefore, the Abstract of this application is not intended to be used to construe the scope of the claims or to limit the scope of the subject matter that is disclosed herein. Moreover, any headings that can be employed herein are also not intended to be used to construe the scope of the claims or to limit the scope of the subject matter that is disclosed herein. Any use of the past tense to describe an example otherwise indicated as constructive or prophetic is not intended to reflect that the constructive or prophetic example has actually been carried out.

While embodiments of the disclosure have been shown and described, modifications thereof can be made without departing from the spirit and teachings of the invention. The embodiments and examples described herein are exemplary only, and are not intended to be limiting. Many variations and modifications of the invention disclosed herein are possible and are within the scope of the invention.

Accordingly, the scope of protection is not limited by the description set out above but is only limited by the claims which follow, that scope including all equivalents of the subject matter of the claims. Each and every claim is incorporated into the specification as an embodiment of the present invention. Thus, the claims are a further description and are an addition to the detailed description of the present invention. The disclosures of all patents, patent applications, and publications cited herein are hereby incorporated by reference.

What is claimed is:

1. A process for producing syngas and olefins comprising:
   (a) feeding a catalytic partial oxidation (CPO) reactant mixture to a CPO reactor; wherein the CPO reactant mixture comprises oxygen, first hydrocarbons, and optionally steam; wherein at least a portion of the CPO reactant mixture reacts, via a CPO reaction, in the CPO reactor to produce a CPO reactor effluent; wherein the CPO reactor comprises a CPO catalyst; wherein the CPO reactor effluent comprises hydrogen ($H_2$), carbon monoxide (CO), carbon dioxide ($CO_2$), water, and unreacted first hydrocarbons, and wherein the CPO reactor effluent is characterized by an M ratio of the CPO reactor effluent, wherein the M ratio is a molar ratio defined as $(H_2-CO_2)/(CO+CO_2)$;
   (b) feeding a cracking unit feed to a cracking unit to produce a cracking unit product stream, a hydrogen-rich stream, and a hydrocarbon recovery stream; wherein the cracking unit feed comprises second hydrocarbons; wherein the first hydrocarbons and the second hydrocarbons are the same or different; wherein the cracking unit product stream comprises olefins; wherein the hydrogen-rich stream comprises hydrogen, methane, and optionally unreacted second hydrocarbons; and wherein the hydrocarbon recovery stream comprises $C_{4+}$ hydrocarbons; and
   (c) contacting at least a portion of the CPO reactor effluent with at least a portion of the hydrogen-rich stream to yield hydrogen-enriched syngas, wherein the hydrogen-enriched syngas is characterized by an M ratio of the hydrogen-enriched syngas, and wherein the M ratio of the hydrogen-enriched syngas is greater than the M ratio of the CPO reactor effluent.

2. The process of claim 1, wherein the first hydrocarbons and/or the second hydrocarbons comprise methane, ethane, propane, butanes, naptha, natural gas, natural gas liquids, associated gas, well head gas, enriched gas, paraffins, shale gas, shale liquids, fluid catalytic cracking (FCC) off gas, refinery process gases, stack gases, fuel gas from fuel gas header, or combinations thereof; and wherein the olefins comprise ethylene.

3. The process of claim 1, wherein the hydrogen-enriched syngas comprises carbon dioxide in an amount of from about 0.25 mol % to about 5 mol %.

4. The process of claim 1, wherein the cracking unit comprises a cracking reactor and a separating unit; and wherein the process further comprises cooling the CPO reactor; wherein cooling the CPO reactor comprises heating the cracking reactor while cooling the CPO reactor by heat transfer between the CPO reactor and the cracking reactor.

5. The process of claim 1, wherein the CPO reactor is characterized by at least one CPO operational parameter selected from the group consisting of a CPO feed temperature of from about 25° C. to about 600° C.; a CPO effluent temperature of from about 300° C. to about 1,600° C.; a CPO pressure of from about 1 barg to about 90 barg; a CPO contact time of from about 0.001 milliseconds (ms) to about 5 seconds (s); a carbon to oxygen (C/O) molar ratio in the CPO reactant mixture of from about 0.5:1 to about 3:1, wherein the C/O molar ratio refers to the total moles of carbon (C) of hydrocarbons in the reactant mixture divided by the total moles of oxygen ($O_2$) in the reactant mixture; a steam to carbon (S/C) molar ratio in the CPO reactant mixture of from about 0.01:1 to less than about 2.4:1, wherein the S/C molar ratio refers to the total moles of water ($H_2O$) in the reactant mixture divided by the total moles of carbon (C) of hydrocarbons in the reactant mixture; and combinations thereof.

6. The process of claim 1, wherein the M ratio of the hydrogen-enriched syngas is equal to or greater than about 1.8.

7. The process of claim 1, wherein the hydrogen-enriched syngas is characterized by a hydrogen to carbon monoxide ($H_2$/CO) molar ratio of greater than about 2.0; and wherein the $H_2$/CO molar ratio of the hydrogen-enriched syngas is greater than the $H_2$/CO molar ratio of the CPO reactor effluent.

8. The process of claim 1, further comprising (i) introducing at least a portion of the hydrogen-enriched syngas to a methanol reactor to produce a methanol reactor effluent stream; wherein the methanol reactor effluent stream comprises methanol, water, hydrogen, carbon monoxide, carbon dioxide, methane, first hydrocarbons, and optionally second hydrocarbons; (ii) separating at least a portion of the methanol reactor effluent stream into a crude methanol stream and a vapor stream; wherein the crude methanol stream comprises methanol and water; and wherein the vapor stream comprises hydrogen, carbon monoxide, carbon dioxide, methane, first hydrocarbons, and optionally second hydrocarbons; (iii) introducing at least a portion of the vapor stream to a first hydrogen recovery unit to produce a hydrogen stream and a residual gas stream, wherein the hydrogen stream comprises at least a portion of the hydrogen of the vapor stream, and wherein the residual gas stream comprises carbon monoxide, carbon dioxide, methane, first hydrocarbons, and optionally second hydrocarbons; (iv) recycling at least a portion of the hydrogen stream to the methanol reactor; and (v) separating at least a portion of the crude methanol stream into a methanol stream and a water stream.

9. The process of claim 8, wherein (1) at least a portion of the residual gas stream is purged, used as fuel, fed to the CPO reactor in step (a), or combinations thereof; and/or (2) at least a portion of the hydrocarbon recovery stream is recycled to the cracking unit, used as fuel, fed to the CPO reactor in step (a), or combinations thereof.

\* \* \* \* \*